(12) United States Patent
Sako et al.

(10) Patent No.: US 8,128,958 B2
(45) Date of Patent: *Mar. 6, 2012

(54) SUSTAINED RELEASE PHARMACEUTICAL COMPOSITION

(75) Inventors: Kazuhiro Sako, Shizuoka-ken (JP);
Toyohiro Sawada, Shizuoka-ken (JP);
Hiromu Kondo, Shizuoka-ken (JP);
Keiichi Yoshihara, Shizuoka-ken (JP);
Hiroyuki Kojima, Shizuoka-ken (JP)

(73) Assignee: Astellas Pharma Inc., Tokyo (JP)

( * ) Notice: Subject to any disclaimer, the term of this patent is extended or adjusted under 35 U.S.C. 154(b) by 1105 days.

This patent is subject to a terminal disclaimer.

(21) Appl. No.: 10/843,005

(22) Filed: May 10, 2004

(65) Prior Publication Data
US 2005/0100603 A1 May 12, 2005

(30) Foreign Application Priority Data
Nov. 10, 2003 (JP) .................. 2003-380448

(51) Int. Cl.
*A61K 9/20* (2006.01)
*A61K 9/16* (2006.01)
*A61K 9/22* (2006.01)
*A61K 9/50* (2006.01)
*A01N 41/06* (2006.01)
*C07C 303/00* (2006.01)

(52) U.S. Cl. ........ 424/468; 424/464; 424/465; 424/485; 424/488; 424/489; 424/499; 424/500; 514/601; 564/80; 564/84

(58) Field of Classification Search .................. 424/450, 424/468, 464, 465; 514/602
See application file for complete search history.

(56) References Cited

U.S. PATENT DOCUMENTS

| | | | |
|---|---|---|---|
| 4,772,475 A * | 9/1988 | Fukui et al. .................. | 424/468 |
| 5,843,472 A | 12/1998 | Ma et al. | |
| 6,436,441 B1 | 8/2002 | Sako et al. | |
| 6,562,375 B1 * | 5/2003 | Sako et al. .................. | 424/486 |
| 7,387,793 B2 | 6/2008 | Venkatesh et al. | |
| 2003/0104048 A1 * | 6/2003 | Patel et al. .................. | 424/451 |
| 2003/0147950 A1 | 8/2003 | Platteeuw et al. | |
| 2003/0147955 A1 | 8/2003 | Platteeuw et al. | |
| 2004/0067908 A1 | 4/2004 | Nakade et al. | |
| 2004/0091528 A1 * | 5/2004 | Rogers et al. .................. | 424/468 |
| 2004/0213845 A1 | 10/2004 | Sugihara | |
| 2005/0053653 A1 * | 3/2005 | Kidane et al. .................. | 424/463 |
| 2005/0100603 A1 | 5/2005 | Sako et al. | |
| 2005/0100606 A1 * | 5/2005 | Wang et al. .................. | 424/470 |

FOREIGN PATENT DOCUMENTS

| | | |
|---|---|---|
| CA | 2 419 089 A1 | 3/2003 |
| CA | 2 490 299 A1 | 9/2004 |
| DE | 693 32 081 T2 | 2/2003 |
| DE | 202 20 604 U1 | 4/2004 |
| DE | 20 2004 003 404 U1 | 8/2004 |
| DE | 10333497 | 2/2005 |
| EP | 1088551 | 4/2001 |
| EP | 0661045 B1 | 7/2002 |
| EP | 1523994 A1 | 4/2005 |
| WO | WO 03/039530 | 5/2003 |

OTHER PUBLICATIONS

"Remington: The Science and Practice of Pharmacy," 19th Ed., A.R. Genaro Editor, Mack Publishing (1995).*
Wilde and McTavish, "Tamsulosin," Drugs (1996) 52(6):883-898.*
Djavan and Marberger, "A Meta Analysis on the Efficacy and Tolerability of Alpha-1 Androceptor Agonists in Patients with Lower Urinary Tract Symptoms Suggestive of Benign Prostatic Obstruction," Eur. Urol. (1999) 36:1-13.*
Kay, Allan, Perry, McDonagh, Davy, Storm, Bird and Dewit, "The Clinical Pharmacokinetics of a New Pharmacokinetically Enhanced Formulation of Amoxicillin/Clavulanate," Clinical Therapeutics (2001) 23(4):578-584.*
The Handbook of Pharmaceutical Excipients; American Pharm. Assoc. (1988); pp. 44 (CMC-Ca) and 53 (MCC).*
Website: www.nlm.nih.gov; (National Library of Medicine); chemical nomenclature definition for tamsulosin.*
FLOMAX website; disclosing ingredients (http://www.rxlist.com/flomax-drug.htm); dated Jan. 3, 2011.*
EP Communication Under Rule 71(3) EPC dated Apr. 16, 2008 re Application No. 04013654-1;Applicant: Astellas Pharma Inc., and pending claims.
Chapple, et al., Tamsulosin Oral Controlled Absorption System (OCAS) in Patients with Lower Urinary Tract Symptoms Suggestive of Benign Prostatic Hyperplasia (LUTS/BPH); Efficacy and Tolerability in a Placebo and Active Comparator Comparator Controlled Phase 3a Study; European Urology Supplements 4(2005) 33-44.
Chapple, et al., Tamsulosin Oral Controlled Absorption System (OCAS) in Patients with Lower Urinary Tract Symptoms Suggestive of Benign Prostatic Hyperplasia (LUTS/BPH): Efficacy and Tolerability in a Phase 2b Dose-Response Study; European Urology Supplements 4 (2005) 25-32.
Djavan, et al.; The Impact of Tamsulosin Oral Controlled Adsorption System (OCAS) on Nocturia and the Quality of Sleep: Preliminary Results of a Pilot Study; European Urology Supplements 4 (2005) 61-68.
Michel, et al.; Comparison of Vascular $\alpha_1$-Adrenoceptor Antagonism of Tamsulosin in Oral Controlled Adsorption System (OCAS) and Modified Release (MR) Formulations; European Urology Supplements 4 (2005) 45-52.
Michel, et al.; Cardiovascular Safety of the Oral Controlled Absorption System (OCAS) Formulation of Tamsulosin Compared to the Modified Release (MR) Formulation; European Urology Supplements 4 (2005) 53-60.

(Continued)

*Primary Examiner* — Robert A Wax
*Assistant Examiner* — Jeffrey T Palenik
(74) *Attorney, Agent, or Firm* — Kilpatrick Townsend & Stockton LLP

(57) ABSTRACT

The present invention provides a sustained-release pharmaceutical composition, characterized in that, there are contained tamsulosin or a pharmaceutically acceptable salt thereof and a carrier for a sustained-release pharmaceutical composition and the ratio ($C_{min}/C_{max}$ ratio) of the plasma tamsulosin concentration at 24 hours after the administration of the preparation per os ($C_{min}$) to the maximum plasma tamsulosin concentration after the administration ($C_{max}$) is about 0.4 or more.

14 Claims, 6 Drawing Sheets

OTHER PUBLICATIONS

Michel, et al.; The Pharmacokinetic Profile of Tamsulosin Oral Controlled Absorption System (OCAS); European Urology Supplements 4 (2005) 15-24.

EP Patent Application No. 04013654.1-2123; Office Action dated May 12, 2010 from the Primary Examiner of the EP Patent Office.

Response by Applicants to EP Office Action in App. No. 04013654.1, dated Nov. 22, 2010.

Third Party Observation under Article 115 EPC in App. No. 04013654.1, dated Mar. 27, 2009.

Third Party Observations under Article 115 EPC in App. No. 04013654.1, dated Sep. 19, 2008.

V. W. Steinijans; Pharmacokinetic characterization of controlled-release formulations; European Journal of Drug Metabolism and Pharmacokinetics; 1990; pp. 173-181; vol. 15, No. 2.

Decision as issued by the German Patent and Trademark Office on Dec. 16, 2010, 14 pages (English translation, 13 pages).

Francis, F.J, Ed., *Wiley Encyclopedia of Food Science and Technology, $2^{nd}$ Edition*, John Wiley & Sons Publishing (1999) pp. 1216-1220.

*The Japanese Pharmaceopoeia*, $14^{th}$ *Edition*, Chapter 15: Dissolution Test, last updated on Dec. 19, 2001, located at <http://jpdb.nihs.go.jp/jp14e/>, last accessed on Jan. 31, 2011, pp. 33-36.

Warnke, A. et al., "Schnelle Freisetzung oder Retardformulierung?Verbesserte Therapie durch optimierte Arzneiformen?"*Pharm. Unserer Zeit*, 2004, pp. 456-465.

Kiss, et al. "Tamsulosin Drug Ratio in Prostate Versus Free Fraction in Plasma Supports Pharmacokinetic (PK) Contribution to its Uroselectivity," *The Journal of Urology*, 2003, vol. 169, No. 4, Supplement, p. 288.

Summons to attend oral proceedings pursuant to Rule 115(1) EPC mailed on Feb. 16, 2011, in European patent application No. 04013654.1, 9 pp.

\* cited by examiner

A  B

SUSTAINED RELEASE PHARMACEUTICAL COMPOSITION

CROSS-REFERENCES TO RELATED APPLICATIONS

The present application claims priority to JP 2003-380448, filed Nov. 10, 2003, the teaching of which is hereby incorporated hereby by reference in its entirety for all purposes.

FIELD OF THE INVENTION

Technical Field

The present invention relates to a sustained-release pharmaceutical composition containing tamsulosin or a pharmaceutically acceptable salt thereof. More particularly, the present invention relates to a sustained-release pharmaceutical composition which is characterized in containing tamsulosin or a pharmaceutically acceptable salt thereof and a carrier for sustained-release pharmaceutical composition and showing a specific ratio of the plasma drug concentration at 24 hours after oral administration of the sustained-release pharmaceutical composition to the maximum plasma drug concentration. The present invention also relates to a method for the administration of tamsulosin hydrochloride for reducing the adverse events accompanied by therapy or prevention on the basis of an adrenaline α receptor blocking action.

BACKGROUND OF THE INVENTION

Background Art

Tamsulosin or a salt thereof has been known to have an adrenaline α receptor blocking action and, particularly, its hydrochloride (tamsulosin hydrochloride) has been known to have an α receptor blocking action for urethra and prostate areas and has been widely used as a drug which lowers the prostate pressure of urethral pressure profile and improves urinary disturbance accompanied by prostate-gland enlargement. Recently, its efficacy to an excretion disturbance accompanied by neurogenic bladder and lower uropathy (which is urinary disturbance accompanied by functional obstruction of lower urinary tract and urinary disturbance not accompanied by clear organic disturbance nor neurological abnormality in lower urinary tract) has been confirmed as well (refer, for example, to International Laid-Open Pamphlet No. 00/00187 (corresponding to European Laid-Open Patent No. 1088551 gazette) and International Laid-Open Pamphlet No. 01/10436 (corresponding to European Laid-Open Patent gazette No. 1203582)).

With regard to information on the adverse reactions of tamsulosin hydrochloride, the following information is described in a package insert of the product. Thus, as to the adverse reactions, there are described that, 104 cases (2.2%) of adverse reactions (including abnormal clinical data) presumably related to the present agent were observed among 4724 cases for the results of the research in use upon approval and post marketing surveillance in Japan. There are described that most of them were dizziness and unpleasant feeling of stomach (upon application for re-examination), fainting and unconsciousness (frequency ambiguous) and transient unconsciousness as a result of hypotension happened as a serious adverse reaction and that other adverse reactions were dizziness and unsteady feeling (0.1 to less than 5%), orthostatic syncope, headache and sleepiness (less than 0.1%) and annoyance (frequency ambiguous) in psychoneural area and hypotension, postural hypotension, blood pressure, tachycardia and palpitation (less than 0.1%) and arrhythmia (frequency ambiguous) in circulatory area. There are also described as to pharmacokinetics of tamsulosin that, when 0.1 to 0.6 mg of this agent was orally administered to healthy adult volunteers, plasma concentrations of the unchanged drug showed a peak at 7 to 8 hours after the administration and its half-life was 9.0 to 11.6 hours, that $C_{max}$ and AUC was increased almost in proportion to the dose administered and that, when this agent was repeatedly administered per os for seven days, although the half-life became somewhat prolonged, plasma concentration profiles reached the steady state on day 4.

Tamsulosin is an α receptor blocking agent. When this agent was administered in a form of powder triturated with lactose, adverse reactions such as postural hypotension was induced and, therefore, at present, a once-daily sustained release preparation (Flomax/Harnal/Omnic (all of them are registered trade marks)) where adverse reactions such as postural hypotension is suppressed by use of the multiparticulate sustained-release preparation has been utilized in the actual setting of medicine (refer, for example, to JP-B-7-72129 corresponding to U.S. Pat. No. 4,772,475). The sustained-release preparation utilizing such an art for pharmaceutical preparations is used at the dose of 0.1 mg to 0.2 mg per day in Japan and 0.4 mg to 0.8 mg per day in Europe and America.

With regard to the adverse reactions, erectile and ejaculation disturbance, hypotension, unsteady feeling, etc. were reported to an extent of about 5% in Europe and America. Although the current preparation has excellent sustained-release characteristics, which reduces the adverse reactions caused by an α receipt blocking actions, the preparation used at present has variation factors such as changes in pharmacokinetics under a fast condition and is to be improved further.

On the other hand, there are α receptor blocking agents such as prazosin, terazosin, alfuzosin, doxazosin. All of those drugs were originally used as hypotensive drugs and, therefore, they show postural hypotension as an adverse reaction, and utilized a gradually increasing method where it takes about 4 to 6 weeks to provide the therapeutic drug levels in plasma, so that they are the drugs which are limited in use and administration in the clinical setting.

With regard to a sustained-release preparation containing an α receptor blocking agent (prazosin or alfuzosin) as mentioned above, the drugs are absorbed poorly in the region of colon, and therefore, since the drug concentration in the plasma extremely lower a controlled release preparation of the drugs which shows so-called zero-order drug release where the drug is released in a sustained matter precisely at a constant rate is not appropriate. Thus, in order to suppress the adverse reactions such as postural hypotension and to achieve a good therapeutic effect, there is described an invention concerning a preparation where the first part of the drug is released in the upper gastrointestinal tract and the second part of the drug is released with a sustained manner in the area of colon (refer, for example, to International Laid-Open Pamphlet No. 94/27582 (corresponding to European Patent Gazette No. 0,700,285). These pharmaceutical preparations enable to compensate for the reduction of drug absorption by means of enhancement of drug release rate in the lower gastrointestinal tract, because of low drug absorption in colon. However, such preparations are based on a time-controlled drug release system and, therefore, it is still necessary to improve in order to enhance the drug absorption in colon. In addition, when the α receptor blocking agent is easily absorbed in the lower area of the gastrointestinal tract such as colon, drug concentrations in plasma becomes high and, accordingly, there is an anxiety of induction of adverse reactions such as severe hypotension whereby improvement therefor is still needed.

On the contrary, with regard to tamsulosin, because clinical development will be expanded in order to obtain other indications of the drug and, therefore, it is also predicted that tamsulosin doses for therapy or prevention will become 0.8 mg or more.

Further, in the current preparation containing tamsulosin hydrochloride, there is a restriction of administration after meals concerning its dosage. However, in view of the life patterns and QOL (quality of life) of businesspersons or aged people at present and compliance for taking drugs, there has been a demand for the development of preparations without restriction for food ingestion in its dosage (there is no food effect on bioavailability).

[Patent Document 1] International Laid-Open Pamphlet No.00/00187

[Patent Document 2] International Laid-Open Pamphlet No.01/10436

[Patent Document 3] JP-B-7-72129

[Patent Document 4] International Laid-Open Pamphlet No. 94/27582

BRIEF SUMMARY OF THE INVENTION

[Problems that the Invention is to Solve]

Accordingly, there has been still a demand for development of a sustained-release pharmaceutical preparation in which, as compared with the current oral sustained-release preparations containing tamsulosin hydrochloride which have been utilized in the medical setting, efficacy is equivalent or even more, adverse events such as adverse reactions (e.g., postural hypotension) are reduced, dose can be increased and, if desired, no restriction of food ingestion in its dosage and also a method for the administration of tamsulosin hydrochloride in which the adverse reactions of tamsulosin accompanied by therapy or prevention on the basis of an α receptor blocking action are reduced.

[Means for Solving the Problems]

In view of the above-mentioned circumstances, the present inventors have at first intensively carried out various investigations using a novel hydrogel sustained-release preparation which has been created by the company of the applicant and, as a result, it has been found that a preparation in which the ratio ($C_{min}/C_{max}$ ratio) of a plasma tamsulosin concentration at 24 hours after administration ($C_{min}$) to the maximum plasma tamsulosin concentration ($C_{max}$) is about 0.4 or more shows equivalent or even better efficacy in a clinical test as compared with the current preparation and further that adverse reactions can be reduced as compared with the current preparation. It has been also found that, regardless of the condition for taking meals, there is no significant difference in pharmacokinetic parameters. The present inventors have also found, in a clinical test conducted for a purpose of developing other indications using the above-mentioned hydrogel-forming preparation, that a preparation containing a high dose of tamsulosin hydrochloride (1.0 mg or 1.5 mg) shows similar adverse effect profiles to those of placebo (a group to which no active ingredient is administered). In spite of the fact that various factors affect on both release profiles from preparations and absorption from gastrointestinal tract for the drug, there is a correlation in many cases between an in vitro drug release time from the preparation and its bioavailability. Establishment of such a correlation has been reported in many patents and papers and a drug release profile has been usually used for illustration of the bioavailability for the drug contained in special preparations. Thus, the drug release time in various preparations is one of important and basic characteristics, which are to be considered when judging whether the drug-releasing property of special preparations is to be evaluated or not in vivo. In sustained-release preparations, dose per administration is usually larger and, in addition, the sustained-release property is achieved on the basis of a special drug release-controlling mechanism. Therefore, it is very important to function the drug-releasing mechanism of preparations in the same manner between in a hungry stage (before ingestion of meal) and after meal (after ingestion of meal) when considering bioequivalence.

Dissolution test has provided supportive data for the evaluation of identity (similarity) of release-controlling mechanism or for the evaluation of bioequivalence among the preparations. Both objects have been thought that, when the release behavior of the preparation is similar, it can be predicted to some extent that in vivo performance is similar in both preparations in a range of within and between subjects variation when administered to the body.

On the basis of the in vitro and in vivo correlation theory, it is thought that, when preparations show similar drug-releasing profile under the same dissolution test condition, the preparations show similar pharmacokinetic parameters when orally administered even if those are preparations on the basis of other technique for pharmaceutical preparation. Accordingly, it can be expected that preparations showing the same pharmacokinetic parameters as the above-mentioned hydrogel-forming preparations have equivalent or even more efficacy as compared with the current preparation and reduce the occurrence of adverse events. In addition, an increase in dose or no restriction for ingestion of food in dosage can be expected. On the basis of such a concept, preparations showing the similar drug release profile as the above-mentioned hydrogel-forming preparations are manufactured whereupon the present invention has been achieved.

Thus, the present invention provides:

1. A sustained-release pharmaceutical composition, characterized in that, there are contained tamsulosin or a pharmaceutically acceptable salt thereof and a carrier for a sustained-release pharmaceutical composition and the ratio ($C_{min}/C_{max}$ ratio) of the plasma tamsulosin concentration at 24 hours after the administration of the preparation per os ($C_{min}$) to the maximum plasma tamsulosin concentration after the administration ($C_{max}$) is about 0.4 or more;

2. The sustained-release pharmaceutical composition according to the above 1, wherein a value of $C_{min}$ normalized by the dose of tamsulosin or a pharmaceutically acceptable salt thereof is more than about $10 \times 10^{-6}$ mL$^{-1}$;

3. The sustained-release pharmaceutical composition according to the above 1 or 2, wherein $C_{min}$ is about 4 ng/mL or more;

4. The sustained-release pharmaceutical composition according to any of the above 1 to 3, wherein a value of $C_{max}$ normalized by the dose of tamsulosin or a pharmaceutically acceptable salt thereof is about $40 \times 10^{-6}$ mL$^{-1}$ or less;

5. The sustained-release pharmaceutical composition according to any of the above 1 to 4, wherein a value of $C_{max}$ normalized by the dose of tamsulosin or a pharmaceutically acceptable salt thereof is about $30 \times 10^{-6}$ mL$^{-1}$ or less;

6. The sustained-release pharmaceutical composition according to any of the above 1 to 5, wherein a value of $C_{max}$ is about 20 ng/mL or less;

7. The sustained-release pharmaceutical composition according to any of the above 1 to 6, wherein its adverse event profiles are not significantly different from those of placebo;

8. The sustained-release pharmaceutical composition according to any of the above 1 to 7, wherein, when it is administered before ingestion of meal or after ingestion of meal, there is no significant difference in pharmacokinetic parameters obtained from plasma tamsulosin concentration profiles;

9. The sustained-release pharmaceutical composition according to any of the above 1 to 8, wherein it is a sustained-release hydrogel-forming preparation;

10. The sustained-release pharmaceutical composition according to any of the above 1 to 8, wherein it is a preparation of an osmotic pump type;

11. The sustained-release pharmaceutical composition according to any of the above 1 to 8, wherein it is a gel preparation where a plurality of gums is combined;

12. The sustained-release pharmaceutical composition according to any of the above 1 to 8, wherein it is a multi-layered tablet comprising a drug layer and release-controlling layer(s) which are geometrically aligned;

13. The sustained-release pharmaceutical composition according to any of the above 1 to 8, wherein it is a preparation which retains in stomach using a swelling polymer;

14. The sustained-release pharmaceutical composition according to any of the above 1 to 8, wherein it is a matrix preparation using a water-soluble polymer;

15. A method where, tamsulosin has been released even for 8 to 24 hours after oral administration of a pharmaceutical composition containing tamsulosin or a pharmaceutically acceptable salt thereof and a carrier for a sustained-release pharmaceutical composition and has been absorbed in vivo so that the effective plasma concentrations of tamsulosin or a pharmaceutically acceptable salt thereof is maintained;

16. The method according to the above 15, wherein tamsulosin or a pharmaceutically acceptable salt thereof and a carrier for a sustained-released pharmaceutical composition are used and the ratio ($C_{min}/C_{max}$ ratio) of the plasma tamsulosin concentration at 24 hours after the administration of the preparation per os ($C_{min}$) to the maximum plasma tamsulosin concentration after the administration ($C_{max}$) is about 0.4 or more;

17. The method according to the above 15 or 16, wherein a value of $C_{min}$ normalized by the dose of tamsulosin or a pharmaceutically acceptable salt thereof is more than about $10 \times 10^{-6}$ mL$^{-1}$;

18. The method according to any of the above 15 to 17, wherein $C_{min}$ is about 4 ng/mL or more;

19. The method according to any of the above 15 to 18, wherein a value of $C_{max}$ normalized by the dose of tamsulosin or a pharmaceutically acceptable salt thereof is about $40 \times 10^{-6}$ mL$^{-1}$ or less;

20. The method according to any of the above 15 to 19, wherein a value of $C_{max}$ normalized by the dose of tamsulosin or a pharmaceutically acceptable salt thereof is about $30 \times 10^{-6}$ mL$^{-1}$ or less;

21. The method according to any of the above 15 to 20, wherein a value of $C_{max}$ is about 20 ng/mL or less;

22. The method according to any of the above 15 to 21, wherein its adverse event profiles are not significantly different from those of placebo;

23. The method according to any of the above 15 to 22, wherein, when it is administered before ingestion of meal or after ingestion of meal, there is no significant difference in pharmacokinetic parameters obtained from plasma transition concentration profiles;

24. The method according to any of the above 15 to 23, wherein the pharmaceutical composition comprising tamsulosin or a pharmaceutical salt thereof and a carrier for a sustained-release pharmaceutical composition is a sustained-release hydrogel-forming preparation;

25. The method according to any of the above 15 to 23, wherein the pharmaceutical composition comprising tamsulosin or a pharmaceutical salt thereof and a carrier for a sustained-release pharmaceutical composition is a preparation of an osmotic pump type;

26. The method according to any of the above 15 to 23, wherein the pharmaceutical composition comprising tamsulosin or a pharmaceutical salt thereof and a carrier for a sustained-release pharmaceutical composition is a gel preparation where a plurality of gums is combined;

27. The method according to any of the above 15 to 23, wherein the pharmaceutical composition comprising tamsulosin or a pharmaceutical salt thereof and a carrier for a sustained-release pharmaceutical composition is a multi-layered tablet comprising a drug layer and release-controlling layer(s) which are geometrically aligned; and 28. The method according to any of the above 15 to 23, wherein the pharmaceutical composition comprising tamsulosin or a pharmaceutical salt thereof and a carrier for a sustained-release pharmaceutical composition is a preparation which retains in stomach using a swelling polymer;

29. The method according to any of the above 15 to 23, wherein the pharmaceutical composition comprising tamsulosin or a pharmaceutical salt thereof and a carrier for a sustained-release pharmaceutical composition is a matrix preparation using a water-soluble polymer.

DETAILED DESCRIPTION OF THE INVENTION

Figure 1:
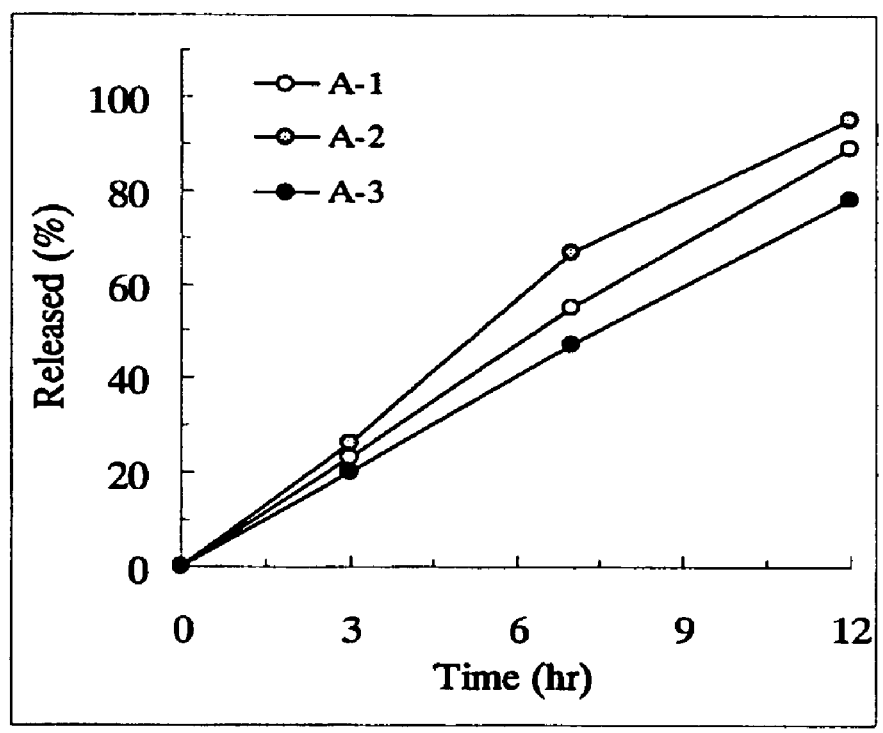
FIG. 1 This is a drawing which shows a releasing characteristic of the drug from each preparation of Example A.
Figure 2:
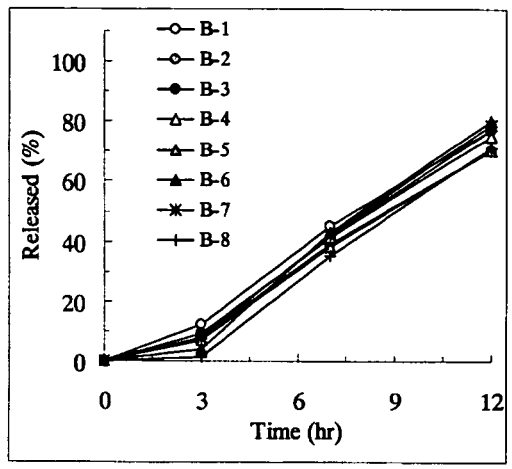
FIG. 2 This is a drawing which shows a releasing characteristic of the drug from each preparation of Example B.
Figure 2:
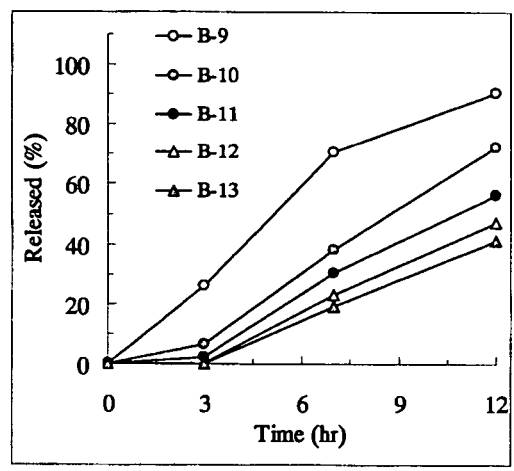
Figure 3:
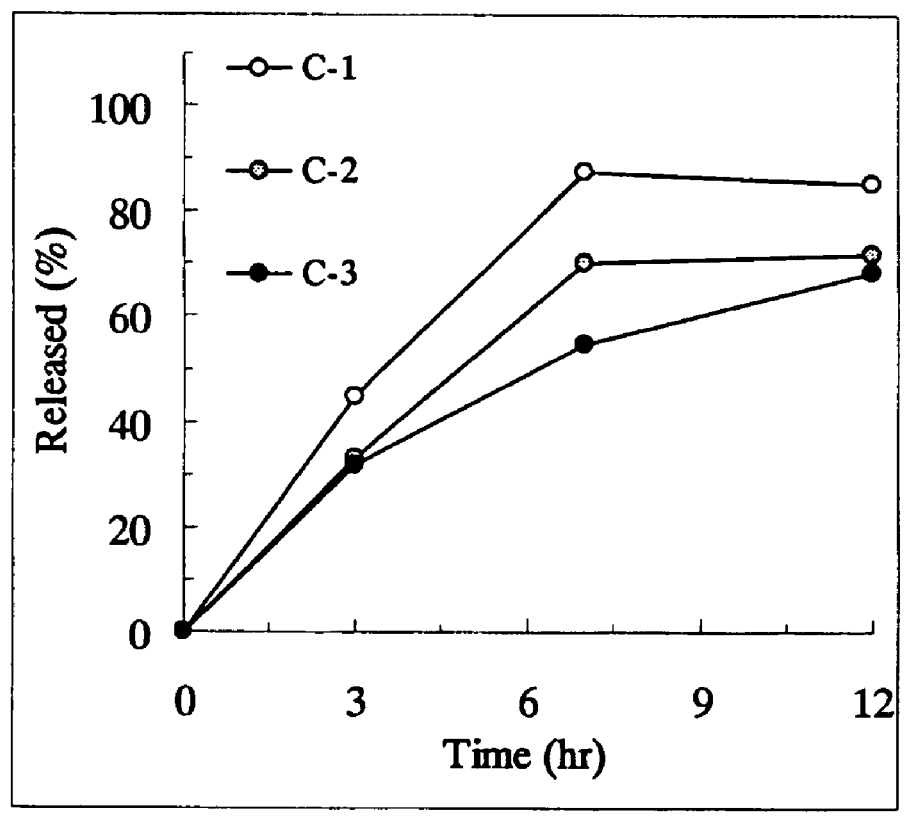
FIG. 3 This is a drawing which shows a releasing characteristic of the drug from each preparation of Example C.
Figure 4:
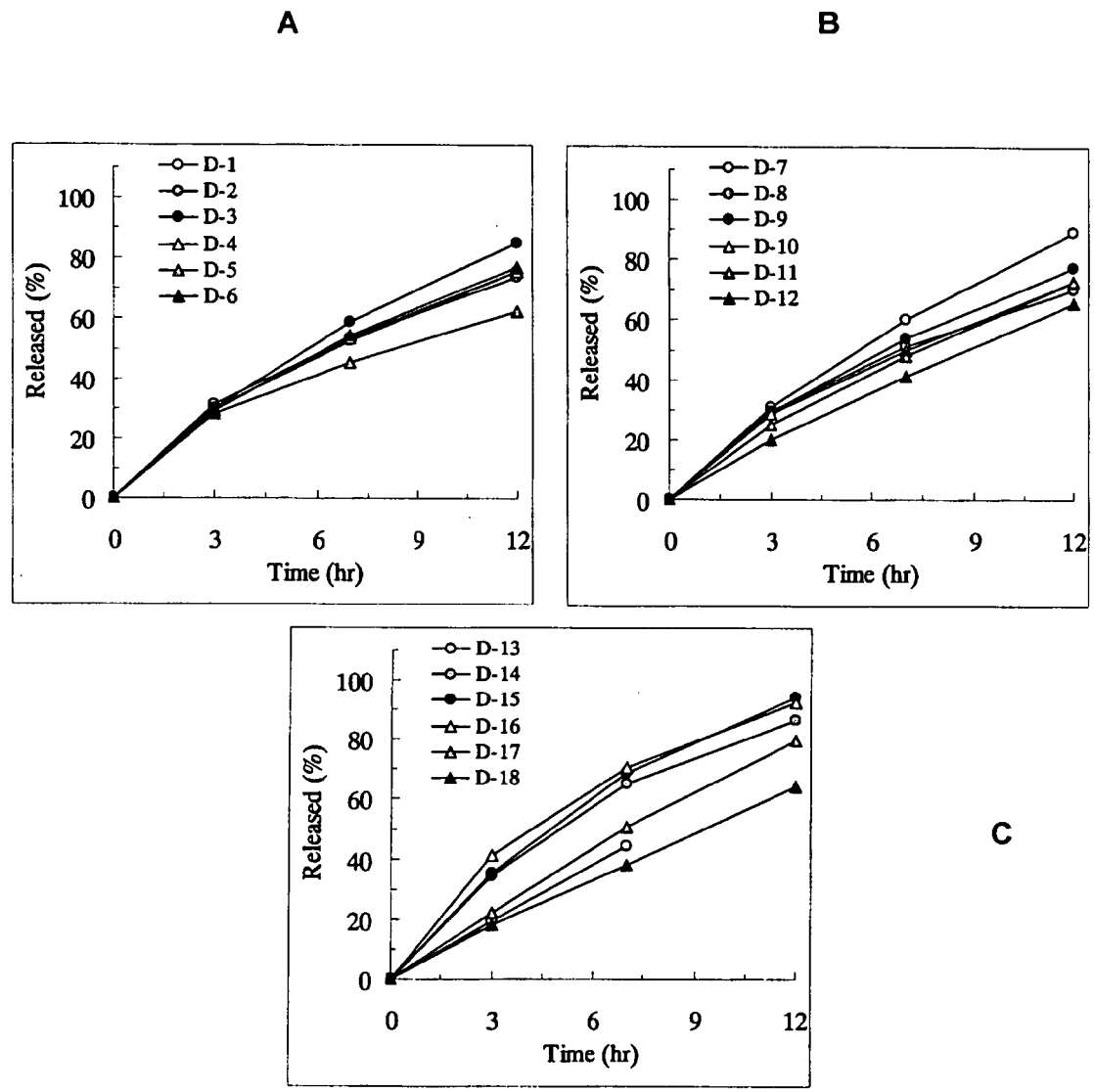
FIG. 4 This is a drawing which shows a releasing characteristic of the drug from each preparation of Example D.
Figure 5:
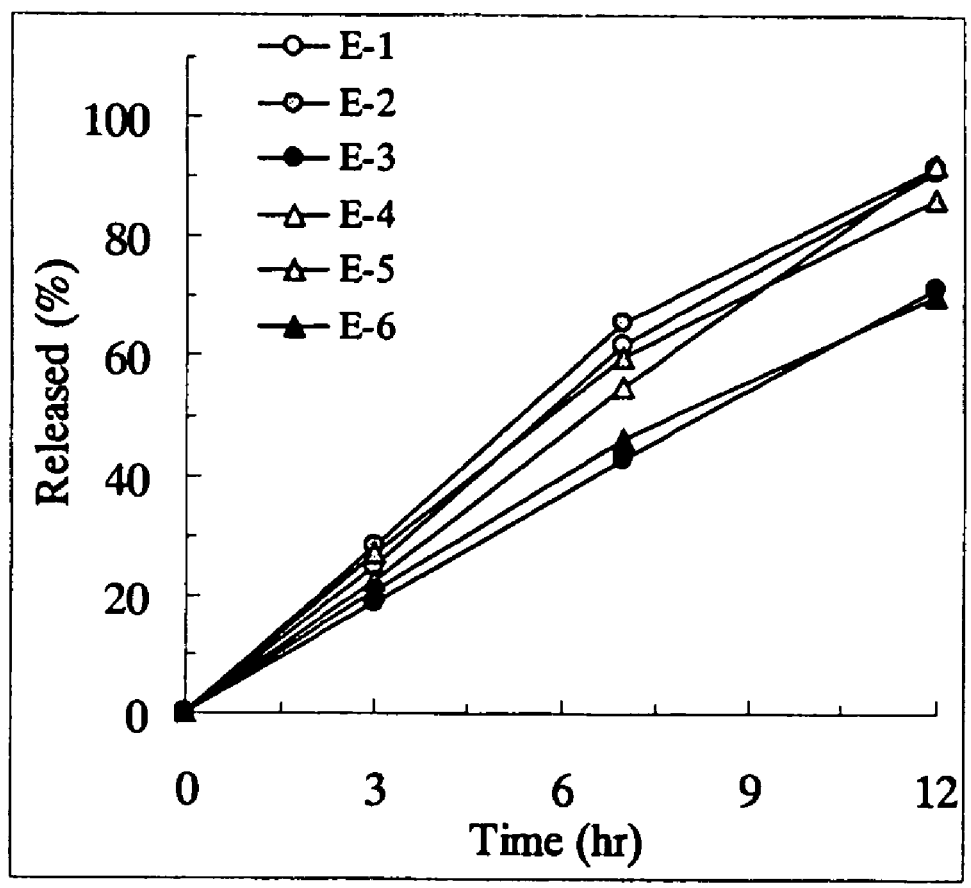
FIG. 5 This is a drawing which shows a releasing characteristic of the drug from each preparation of Example E.
Figure 6:
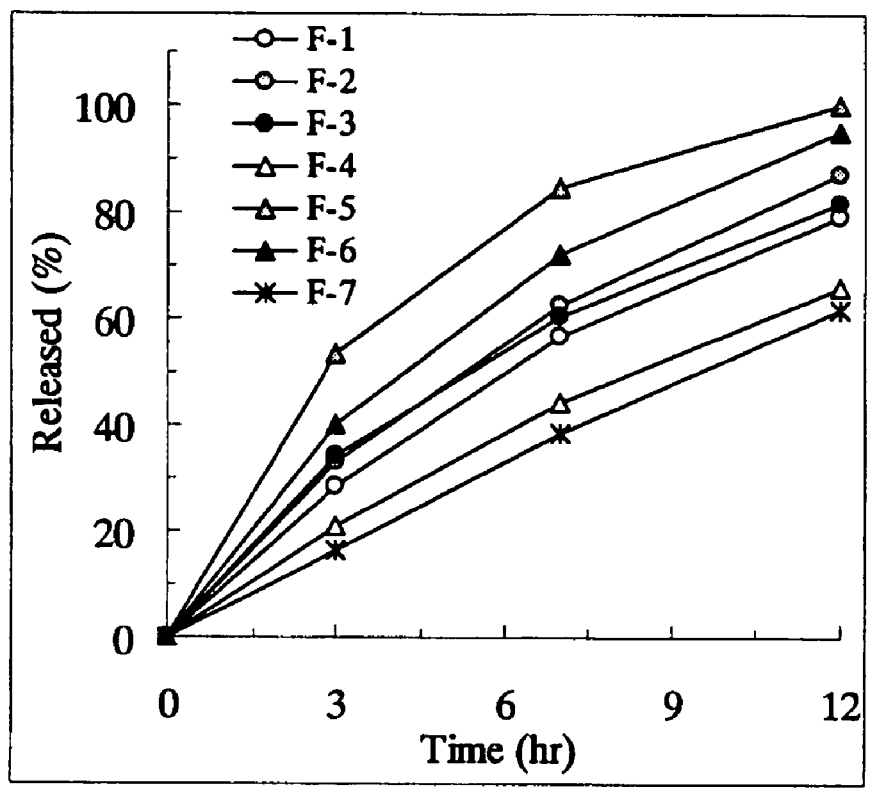
FIG. 6 This is a drawing which shows a releasing characteristic of the drug from each preparation of Example F.

The term "$C_{max}$" means a maximum plasma drug concentration obtained after a unit preparation is administered in vivo.

The term "$C_{min}$" means a plasma drug concentration obtained at 24 hours after a unit preparation is administered in vivo.

The term "AUC" means an area under the curve of a plasma drug concentration profile versus time obtained after a unit preparation is administered in vivo.

The term "pharmacokinetic parameter" means $C_{max}$, AUC, time for reaching at the maximum plasma concentration ($T_{max}$), etc. determined from the plasma drug concentration profiles obtained after administration of a unit preparation in vivo.

The term "sustained-release" means that tamsulosin or a pharmaceutically acceptable salt thereof is released with a sustained manner in such a mode that the plasma tamsulosin concentrations range in an effective level for therapy or prevention of diseases on the basis of an α receptor blocking action during about 6 to 8 hours or even more such as not shorter than 12 hours.

The term "dosage" means a method of use of a sustained-release pharmaceutical preparation containing tamsulosin or a pharmaceutically acceptable salt thereof and a carrier for a sustained-release pharmaceutical composition to patients for therapy or prevention of certain diseases on the basis of an adrenaline receptor blocking action. For example, the term "administered after meal" means administration after about 30 minutes from ingestion of the meal. "Having no restriction for food" means that, when a preparation having, for example, no food effect on bioavailability regardless of ingestion of meals is administered, there is no restriction for administration of the preparation such as that to be administered after meal (about 30 minutes after ingestion of the meal) or to be administered before meal (about 30 minutes before ingestion of the meal). "Administered under a fast condition" means to be administered without ingestion of food at least for 8 hours.

The term "bioequivalent" means that a 90% confidence interval of ratio of the mean value of a test preparation to those of a reference preparation concerning AUC and $C_{max}$ is within a range of 80 to 125%.

The term "adverse reaction" means an action which is the effect inherent to tamsulosin used for therapy or prevention of the diseases on the basis of an adrenaline receptor blocking action.

The "bioavailability" means rate and extent of unchanged substance or active metabolite coming into systemic circulation.

The term "bioequivalent preparation" means a preparation where its bioavailability is equivalent.

[Advantage of the Invention]

As compared with the current oral sustained-release preparation containing tamsulosin hydrochloride which is now provided to clinical setting, the sustained-release pharmaceutical preparation of the present invention and a method for the administration of tamsulosin have equivalent or even more efficacy and, further, reduce the adverse events such as adverse reactions (e.g., postural hypotension). In addition, they are the composition and the administering method with excellent effects that their doses can be increased and that there is no restriction for ingestion of meals. Therefore, the sustained-release pharmaceutical composition and the administering method of the present invention are highly useful as a sustained-release preparation containing tamsulosin hydrochloride for oral use and a method.

BEST MODE FOR CARRYING OUT THE INVENTION

The sustained-release pharmaceutical composition of tamsulosin or a pharmaceutical acceptable salt thereof for oral use in accordance with the present invention will now be illustrated in detail as hereunder.

The pharmaceutical composition of the present invention is characterized with a specific $C_{min}/C_{max}$. As a result of adoption of such a characteristic feature, the sustained-release pharmaceutical composition of the present invention releases tamsulosin or a pharmaceutically acceptable salt thereof with a sustained manner so that plasma tamsulosin concentrations are made within an effective range for therapy or prevention of diseases on the basis of an α receptor blocking action whereby it would be effective for reducing of adverse reactions.

Tamsulosin is (R)(−)-5-[2-[[2-(o-ethoxyphenoxy)ethyl]-amino]propyl]-2-methoxybenzenesulfonamide and is represented by the following structural formula.

[Chem. 1]

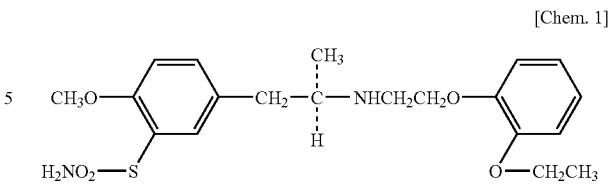

It has been known that tamsulosin or its pharmaceutical acceptable salt thereof has an α receptor blocking action and, particularly, its hydrochloride (tamsulosin hydrochloride) has an α receptor blocking action in urethra and prostate and has been commonly used as a drug for the improvement of urinary dysfunction associated with benign prostatic hyperplasia by reducing the prostatic pressure in urethra. Further, tamsulosin hydrochloride is a very useful drug in clinical test, because it has been clinically confirmed to be effective for therapy of lower urinary tract symptoms.

Tamsulosin or a pharmaceutical acceptable salt has been firstly disclosed in JP-A-56-110665. Tamsulosin is able to form pharmaceutically acceptable acid- and base-addition salts with various inorganic and organic acids or bases. Such salts also are included in the present invention. Examples of such salts are salts with inorganic acids such as hydrochloric acid, sulfuric acid and phosphoric acid; salts with organic acids such as fumaric acid, malic acid, citric acid and succinic acid; salts with alkaline metals such as sodium and potassium; salts with alkaline earth metals such as calcium and magnesium; etc. In the present invention, the most preferred one is a hydrochloride. Such salts are able to be produced by common methods.

Dose of tamsulosin or its pharmaceutically acceptable salt may be appropriately decided for each case taking into account administration route, symptom of the disease, age, sex of the patients although there is no particular limitation therefor so far as it is a pharmaceutically effective amount for therapy or prevention of specific diseases. Usually, such a dose is an effective amount for therapy or prevention of the disease on the basis of an α receptor blocking action and it is, for example, 0.1 to 2 mg, preferably 0.1 to 1.5 mg, more preferably 0.1 to 1.2 mg and, still more preferably, 0.4 to 0.8 mg. In improvement for urinary dysfunction associated with benign prostatic hyperplasia, the dose is 0.1 mg to 0.2 mg per day in Japan and 0.4 mg to 0.8 mg per day in Europe and America. When tamsulosin or its pharmaceutically acceptable salt thereof is used for other indications besides urinary dysfunction, dose of more than 0.8 mg up to about 2 mg would be expected.

Tamsulosin or its pharmaceutically acceptable salt thereof used in the present invention is easily available by means of preparation methods mentioned in JP-A-56-110665 and JP-A-62-114952 or by similar preparation methods. Besides the above-mentioned patents, it is also available by means of preparation methods mentioned in International Laid-Open Pamphlet No. 2002/68382, Korean Patent Laid-Open Gazette No. 2002-85278, International Laid-Open Pamphlet No. 2003/35608, International Laid-Open Pamphlet No. 2003/37850 or No. 2003/37851.

With regard to the maximum plasma tamsulosin concentration ($C_{max}$) and pharmaceutically acceptable salt thereof stipulated by the present invention means a maximum plasma concentration when tamsulosin or a pharmaceutically acceptable salt thereof and a carrier for a sustained-release pharmaceutical composition are orally administered and, when tamsulosin at a dose of 0.4 mg is initially administered per os, the value is about 20 ng/mL or less.

When tamsulosin hydrochloride is administered at a dose of 0.4 mg every day, the $C_{max}$ is preferably not more than about 20 ng/mL, more preferably not more than about 16 ng/mL and, still more preferably, not more than about 12 ng/mL. When tamsulosin hydrochloride is administered at a dose of 0.8 mg every day, the $C_{max}$ is preferably not more than about 40 ng/mL, more preferably not more than about 32 ng/mL and, still more preferably, not more than about 24 ng/mL. When tamsulosin hydrochloride is administered at a dose of 1.2 mg every day, the $C_{max}$ is preferably not more than about 60 ng/mL, more preferably not more than about 48 ng/mL and, still more preferably, not more than about 36 ng/mL.

Incidentally, in the current tamsulosin preparation, the maximum plasma concentration when it is orally administered at a dose of 0.4 mg after ingestion of meal is about 10 ng/mL and, when orally administered under a fast condition, the maximum plasma concentration is about 17 ng/mL. It is thought that the maximum plasma concentration and absorption rate of the drug should play a role in the expression of postural hypotension by tamsulosin. With this regard, further sustained release of the drug from a preparation is useful as well.

Usually, the maximum plasma concentration after oral administration depends upon the dose of a drug. The value $[C_{max}/(dose)]$ where $C_{max}$ as stipulated by the present invention is divided by dose of tamsulosin or a pharmaceutically acceptable salt thereof is a value where $C_{max}$ is normalized by dose and is thought to be a useful parameter for considering an in vivo pharmacokinetics of the drug upon administration at a plurality of doses. When preparations of the present invention are orally administered, the value $[C_{max}/(dose)]$ is not more than about $40 \times 10^{-6}$ mL$^{-1}$. Preferably, it is not more than about $30 \times 10^{-6}$ mL$^{-1}$. When the value is more than that, there is a risk of occurrence of adverse reactions such as postural hypotension.

The minimum plasma concentration of tamsulosin and a pharmaceutically acceptable salt thereof stipulated by the present invention ($C_{min}$) means a plasma concentration of tamsulosin at 24 hours after oral administration of tamsulosin or a pharmaceutically acceptable salt thereof together with a carrier for a sustained-release pharmaceutical composition and is noted as $C_{min}$ (ng/mL). In the tamsulosin, the $C_{min}$ is not less than about 4 ng/mL. Significance of the value is based on the clinical findings which were confirmed with regard to efficacy and adverse reactions in many clinical cases. For example, when tamsulosin hydrochloride is orally administered at a dose of 0.4 mg in a sustained release preparation as an agent for improvement of urinary disturbance accompanied by prostatism, the $C_{min}$ is about 4 ng/mL or more. The $C_{min}$ varies depending upon the dose of the drug. The value $[C_{min}/(dose)]$ where $C_{min}$ as stipulated by the present invention is divided by a dose of tamsulosin or a pharmaceutically acceptable salt thereof is a value where $C_{min}$ is normalized by dose and is thought to be a useful parameter for considering an in vivo pharmacokinetics of the drug upon administration at a plurality of doses. When preparations of the present invention are orally administered, the value $[C_{min}/(dose)]$ is not less than about $10 \times 10^{-6}$ mL$^{-1}$. When the value is less than that, there is a risk that a sufficient pharmacological effect for using as a therapeutic agent for urinary disturbance accompanied by prostatism is not expected.

In tamsulosin and a pharmaceutically acceptable salt thereof, the ratio of the minimum plasma tamsulosin concentration to the maximum plasma tamsulosin concentration is expressed as $C_{min}/C_{max}$. The $C_{min}/C_{max}$ stipulated by the present invention ranges from about 0.4 to less than about 1. When the $C_{min}/C_{max}$ is less than about 0.4, adverse reactions such as postulate hypotension which is noted by administration of the current preparation under a fast condition may occur.

Incidentally, the $C_{min}/C_{max}$ in the current tamsulosin preparation is about 0.222±0.015 under a fast condition and is about 0.355±0.113 after ingestion of meal.

As mentioned above, with regard to the range of plasma tamsulosin concentrations, there is no particular limitation provided that tamsulosin or a pharmaceutically acceptable salt thereof which functions as an active substance, maintains plasma level which are pharmacologically effective for therapy or prevention of the disease when a pharmaceutical composition containing tamsulosin or a pharmaceutically acceptable salt thereof and a carrier for a sustained-release pharmaceutical preparation is orally administered.

With respect to a determination of tamsulosin hydrochloride concentration in human plasma dialysate, there is no particular limitation so far as tamsulosin hydrochloride concentration in human plasma is determined. Examples are methods described in the following:

1. Yoshiaki Soeishi et al., "Sensitive, method for the determination of amsulosin in human plasma using high-performance liquid chromatography with fluorescence detection", Journal of Chromatography B: Biomedical Sciences and Applications, Vol. 533, 1990, pp. 291-296, 2. Hiroshi Matsushima et al., "Highly sensitive method for the determination of tamsulosin hydrochloride in human plasma dialysate, plasma and urine by high-performance liquid chromatography-electrospray tandem mass spectrometry", Journal of Chromatography B: Biomedical Sciences and Applications, Vol. 695, 2, 1997, pp. 317-327.

In more detail example is the following method:

Blood samples are obtained from each subject for the determination of tamsulosin at predetermined time. Plasma samples are collected by centrifugation at about 4° C. for 10 min at 1500 g (3500 rpm) and stored at -70° C. until analysis. These samples are analyzed for their content of tamsulosin according to the method based on liquid-liquid extraction followed by reversed phase HPLC. Final detection is performed using a fluorescence spectrometer.

With regard to a carrier for a sustained-release pharmaceutical composition for oral use together with tamsulosin or a pharmaceutically acceptable salt thereof, there is no particular limitation so far as it is a carrier, a pharmaceutical preparation or a pharmaceutical technique which maintains effective plasma tamsulosin concentrations which is effective for therapy or prevention of diseases. Examples of the carrier (or the pharmaceutical preparation or the pharmaceutical technique) constituting such compositions and components are (A) a sustained-release hydrogel-forming preparation, where the preparation is gelled almost completely during its residence in stomach and small intestine of the upper areas of the gastrointestinal tract, having a drug releasing ability even in colon of the a lower area of the gastrointestinal tract, (B) a preparation of an osmotic pump type, (C) a gel preparation in which a plurality of gums are combined, (D) a multi-layered tablet preparation comprising geometrically-aligned drug layer and release-controlling layer(s), (E) an intragastrically residing preparation using a swelling polymer, (F) a matrix preparation using a water-soluble polymer, etc. All compositions or techniques for pharmaceutical preparation concerning such techniques for pharmaceutical preparation are incorporated in the present invention.

(A) Sustained-Release Hydrogel-Forming Preparation

A carrier used here for the sustained-release pharmaceutical composition comprises an additive by which water is permeated into the inner area of the preparation (which may also be called gelling agent, agent for promotion of gelation or hydrophilic base and, in the present specification, that will be abbreviated as a "hydrophilic base") and a polymer substance which forms hydrogel (a hydrogel-forming polymer).

With regard to the "hydrophilic base", there is no particular limitation so far as it is able to be dissolved before the hydrogel-forming polymer used for the pharmaceutical preparation is gelled. With regard to such a hydrophilic base, the preferred one is that where amount of water necessary for dissolving 1 g of the substrate is not more than 5 ml (20±5° C.) or more preferred one is that where the amount is not more than 4 ml (at the same temperature) and the higher the solubility in water, the higher the effect of permeation of water into the preparation. Examples of such a hydrophilic base are polymers having a high solubility in water such as polyethylene glycol (PEG: for example, PEG 400, PEG 1500, PEG 4000, PEG 6000 and PEG 20000 (trade names) (manufactured by NOF)); sugar alcohols such as D-sorbitol and xylitol; saccharides such as sugar, anhydrous maltose, D-fructose, dextran (for example, Dextran 40) and glucose; surfactants such as polyoxyethylene hydrogenated castor oil (HCO: for example, Cremophor RH 40 (manufactured by BASF) and HCO-40 and HCO-60 (manufactured by Nikko Chemicals)), polyoxyethylene polyoxypropylene glycol (for example, Pluronic F 68 (manufactured by Asahi Denka)) and polyoxyethylene sorbitan higher fatty acid ester (Tween: for example, Tween 80 (manufactured by Kanto Kagaku)); salts such as sodium chloride and magnesium chloride; organic acids such as citric acid and tartaric acid; amino acids such as glycine, β-alanine and lysine hydrochloride; and amino sugar such as meglumine. Examples of the particularly preferred ones are PEG 6000, PVP and D-sorbitol. With regard to the hydrophilic base for the pharmaceutical composition, one component may be used or two or more ones may be used jointly.

The ratio of the hydrophilic base in the preparation is dependent upon characteristics (such as solubility and therapeutic effect) and amount of the drug contained therein, solubility of the hydrophilic base, characteristic of the hydrogel-forming polymer, state of a patient upon administration, etc. and it is preferred to be in such a ratio that the preparation is able to be gelled almost completely during the preparation retains in the upper area of the gastrointestinal tract. Although the residence time of the preparation in the upper area of the gastrointestinal tracts varies depending upon species and also between individuals, it is about 2 hours in dogs and 4 to 5 hours in humans after administration (*Br. J. Clin. Pharmac.*, (1988), 26, 435-443). Therefore, in humans, the preparation can be gelled preferably almost completely within 4 to 5 hours after administration. In general, the ratio of hydrophilic base is about 5 to 80% by weight or, preferably, about 5 to 60% by weight to the whole preparation. With regard to the amount of the hydrophilic base, the gelation does not proceed to the inner area and the release in colon is not sufficient when the amount is insufficient. On the other hand, when the hydrophilic base is too much, the gelation proceeds within short time but resultant gels are easily disintegrated and rapid drug release is observed whereby there is a possibility that a sufficient sustained release is not achieved. In addition, due to much amount of the substrate, there is a disadvantage that size of the preparation itself becomes larger.

It is necessary for the hydrogel-forming polymers used here that to have the physical characteristics, inclusive of viscosity in the enough gelled preparation which can withstand the force generated by contracting movement of the gastrointestinal tract in digestion of food and is able to move to colon of the a lower area of the gastrointestinal tract without destruction of a shape of the preparation.

With regard to the hydrogel-forming polymer used here, that which has a high viscosity upon gelling is preferred. For example, viscosity of a 1% aqueous solution thereof at 25° C. is not less than 1,000 cps is particularly preferred. Incidentally, property of the polymer substance is also dependent upon its molecular weight (weight-average molecular weight) and, with regard to the polymer substance which forms hydrogel applicable to the preparation, the substance having higher molecular weight is preferred and that having an average molecular weight of not less than 2,000,000 is preferred or that having an average molecular weight of not less than 4,000,000 is more preferred. Examples of such a polymer substance are polyethylene oxide (PEO) having a molecular weight of not less than 2,000,000 and, in terms of trade names, they are, for example, Polyox WSR-303, a trade name (average molecular weight: 7,000,000; viscosity: 7500 to 10000 cps (1% aqueous solution at 25° C.)), Polyox WSR Coagulant (average molecular weight: 5,000,000; viscosity: 5500 to 7500 cps (the same condition)), Polyox WSR-301 (average molecular weight: 4,000,000; viscosity: 1650-5500 cps (the same condition)), Polyox WSR-N-60K (average molecular weight: 2,000,000; viscosity: 2000 to 4000 cps (2% aqueous solution at 25° C.)) (all manufactured by Union Carbide), hydroxypropyl methylcellulose (HPMC) (in trade names such as Metolose 90 SH 100000 (viscosity: 4100 to 5600 cps (1% aqueous solution at 20° C.)), Metolose 90SH 50000 (viscosity: 2900 to 3900 cps (the same condition)) and Metolose 90 SH 30000 (viscosity: 25000 to 35000 cps (2% aqueous solution at 20° C.)) all manufactured by Shinetsu Chemical), carboxymethylcellulose sodium (CMC-Na) (in trade names such as San Rose F-15 OMC (average molecular weight: 200,000; viscosity: 1200 to 1800 cps (1% aqueous solution at 25° C.)), San Rose F-i 000 MC (average molecular weight: 420,000; viscosity: 8000 to 12000 (the same condition)) and San Rose F-300 MC (average molecular weight: 300,000; viscosity: 2500 to 3000 cps (the same condition)) manufactured by Nippon Paper Industries), hydroxyethyl cellulose (HEC) (in trade names such as HEC Daicel SE 850 (average molecular weight: 1,480,000; viscosity: 2400 to 3000 cps (1% aqueous solution at 25° C.)) and HEC Daicel SE 900 (average molecular weight: 1,560,000: viscosity: 4000 to 5000 cps (the same condition)) manufactured by Daicel Chemical Industries) and carboxyvinyl polymer (such as Carbopol 940 (average molecular weight: ca. 2,500,000) manufactured by B. F. Goodrich). Preferred one is PEO having an average molecular weight of not less than 2,000,000. In the sustained release for a long period such as not shorter than 12 hours, polymers having higher molecular weight preferably having an average molecular weight of not less than 4,000,000 or those having higher viscosity preferably having viscosity of 1% aqueous solution of not less than 3000 cps at 25° C. are advantageously listed. With regard to the hydrogel-forming polymer substances as such, one component may be used or two or more ones may be used jointly. A mixture comprising two or more polymer substances and showing the property meeting the above-mentioned property as a whole may also be advantageously used as the hydrogel-forming polymer substance.

In order to show a releasing ability of the drug in colon in humans, it is necessary that, after at least 6 to 8 hours or, preferably, after not shorter than 12 hours from administration, a part of the gelled preparation remains in colon. In order to form a hydrogel preparation having such a property, it is preferred that, generally in the preparation of not more than 600 mg per tablet, the ratio of the hydrogel-forming polymer substance to the whole preparation is 10 to 95 w/w% or, preferably, 15 to 90 w/w% and its amount per tablet of the preparation is not less than 70 mg per tablet or, preferably, not less than 100 mg per tablet although that varies depending on size of the preparation, type of the polymer substance, amount and property of the additive for water penetration into the drug and the tablets, etc. When the amount is less than the above, the preparation cannot withstand erosion in the gastrointestinal tract during long term traveling whereby there is a possibility that a sufficient sustained release is not achieved.

When polyethylene oxide is used as a hydrogel-forming polymer, yellow ferric oxide and/or red ferric oxide are/is added thereto in such an amount that does not change the releasing characteristic of the drug with a lapse of time.

Yellow ferric oxide or red ferric oxide may be used either solely or jointly.

With regard to the ratio of yellow ferric oxide and/or red ferric oxide in the preparation, there is no particular limitation so far as it is in such an amount that a controlled-release matrix preparation is stabilized and its drug-releasing characteristic is not changed thereby. Such a rate to the whole preparation is preferably 1 to 20 w/w % and, more preferably, 3 to 15 w/w %. In the "physical mixture in matrix" of yellow ferric oxide and/or red ferric oxide, it is preferably 1 to 20 w/w % or, more preferably, 3 to 15 w/w % to the whole preparation. For example, in the red ferric oxide, it is preferably 5 to 20 w/w % or, more preferably, 10 to 15 w/w % to the whole preparation. In the yellow ferric oxide, it is preferably 1 to 20 w/w % and, more preferably, 3 to 10 w/w %. When yellow ferric oxide and/or red ferric oxide are/is utilized by means of "film coat", it is preferably 0.3 to 2% and, more preferably, 0.5 to 1.5% to the weight of the tablet. At that time, the concentration of yellow ferric oxide or red ferric oxide in the film is preferably 5 to 50% and, more preferably, 10 to 20%.

The term "physical mixture in a matrix" used here stands for a means where, for example, drug, polyethylene oxide and the above-mentioned ferric oxide are uniformly dispersed so that the drug and the ferric oxide are uniformly dispersed in PEO which is a main substrate of the release-controlling component. The term "film coat" stands for that, for example, the above-mentioned ferric oxide is dissolved or suspended in a water-soluble polymer solution such as hydroxypropyl methyl cellulose and is coated on separately-prepared tablet as a thin film. Usually, the yellow ferric oxide and/or the red ferric oxide may be present in any area in the preparation. For example, it may be present in film such as a film coat, in the granules after granulation or in a matrix (such as near polyethylene oxide), etc.

With regard to a method for the manufacture of such a sustained-release pharmaceutical preparation, there is no particular limitation so far as it is a method by which a common hydrogel-forming preparation is able to be prepared. For example, a compression tableting method where drug, hydrophilic base and hydrogel-forming polymer substance together, if necessary, with additive(s) such as yellow ferric oxide and/or red ferric oxide are mixed and subjected to a compression, a capsule compression-filling method, an extrusion molding method where a mixture is fused, solidified and molded, an injection molding method, etc. may be listed. It is also possible that, after molding, a coating treatment such as a common sugar-coating and film coating is applied. It is further possible to fill in a capsule after molding.

(B) An Osmotic Pump Type Preparation:

An osmotic pump type preparation is a preparation where osmotic pressure is utilized to generate a driving force for permeation of liquid into a preparation passing through a semipermeable membrane which allows a free diffusion of liquid but does not allow a free diffusion of drug or osmagent. Therefore, action of the osmotic pressure system has characteristics in such a respect that the drug release can be sustained without pH-dependency at a constant rate for long time even under the circumstances having different pH values during the gastrointestinal transit.

Such a preparation is reported by Santus and Baker, "Osmotic drug delivery: a review of the patent literature" in *Journal of Controlled Release,* 35, p. 1-21 (1995). The preparation is also mentioned in U.S. Pat. Nos. 3,845,770, 3,916,899, 3,995,631, 4,008,719, 4,111,202, 4,160,020, 4,327,725, 4,519,801, 4,578,075, 4,681,583, 5,019,397 and 5,156,850 and all of the contents mentioned in those specifications are incorporated in the present specification.

An osmotic pressure pump type preparation has a two-layered compressed core comprising a drug layer containing tamsulosin or a pharmaceutically acceptable salt thereof (preferably, a hydrochloride) and a push layer coated with a semipermeable membrane which permeates water and external liquids but does not permeate drug, osmagent or osomopolymer, etc. The semipermeable membrane is equipped with at least one drug delivery orifice for connecting the inner area of the preparation to the external environment. Therefore, an osmotic pump type preparation has a mechanism that, after it is administered per os, liquid such as water permeates through the semipermeable membrane into the inner area of the preparation and, due to the resulting osmotic action, tamsulosin is released in a sustained manner at a constant rate for long time through the drug delivery orifice.

The drug layer contains tamsulosin or a pharmaceutically acceptable salt thereof (preferably, a hydrochloride) in a state of mixture with selected additives.

As will be illustrated in detail as hereinafter, the push layer contains an osmotic active component or osmotic active components but does not contain tamsulosin or a pharmaceutically acceptable salt thereof. The osmotic pressure component or the osmotic pressure components is/are representatively composed of an osmagent and one or more osmopolymer(s). The term "osmopolymer" used here stands for a polymer having a relatively big molecular weight showing a swelling upon absorption of liquid so as to release tamsulosin through a drug delivery orifice.

With regard to the semipermeable membrane used here, there is no particular limitation so far as it has a high permeability for external liquids such as water and body fluids but is substantially impermeable for tamsulosin, osmagent, osomopolymer, etc. Such a semipermeable membrane is inherently non-erosive and is insoluble in the body.

Semipermeable homopolymer, semipermeable copolymer, etc. may be listed with regard to the polymer used for the formation of semipermeable membrane. With regard to a material for the polymer as such, a polymer of a cellulose type such as cellulose ester, cellulose ether and cellulose ester-ether may be used. With regard to the polymer of a cellulose type, that where degree of substitution (DS) of an anhydroglucose unit is more than 0 and not more than 3 is used. The degree of substitution (DS) stands for an average number of hydroxyl group being originally present on the anhydroglucose unit which is substituted with a substituent or converted to another group. The anhydroglucose unit may be partially or completely substituted with a group such as acyl, alkanoyl, alkenoyl, aroyl, alkyl, alkoxy, halogen, carboalkyl, alkyl carbamate, alkyl carbonate, alkyl sulfonate, alkyl sulfamate and semipermeable polymer-forming group (here, the organic moiety contains 1 to 12 carbon atom(s) or, preferably, 1 to 8 carbon atom(s)).

With regard to the semipermeable composition, one or more member(s) selected from a group representatively consisting of cellulose acylate, cellulose diacylate, cellulose triacylate, cellulose acetate, cellulose diacetate, cellulose triacetate, mono-, di- and tri-cellulose alkanylate, mono-, di- and tri-alkenylate, mono-, di- and tri-aroylate, etc. is/are used. Representative polymers are cellulose acetate with 1.8 to 2.3 of a DS and 32 to 39.9% of an acetyl content, cellulose diacetate with 1 to 2 of a DS and 21 to 35% of an acetyl content, cellulose triacetate with 2 to 3 of a DS and 34 to 44.8% of an acetyl content, etc. More specific polymers of a cellulose type are cellulose propionate with 1.8 of a DS and 38.5% of a propionyl content, cellulose acetate propionate with 1.5 to 7% of an acetyl content and 39 to 42% of an acetyl content, cellulose acetate propionate with 2.5 to 3% of an acetyl content, 39.2 to 45% of an average propionyl content and 2.8 to 5.4% of a hydroxyl content, cellulose acetate butyrate with 1.8 of a DS, 13 to 15% of an acetyl content, 34 to 39% of a butyryl content 2 to 29% of an acetyl content, 17 to 53% of a butyryl content and 0.5 to 4.7% of a hydroxyl content, cellulose triacylate with 2.6 to 3 of a DS (such as cellulose trivalerate, cellulose trilamate, cellulose tripalmitate, cellulose trioctanoate and cellulose tripropionate), cellulose diester with 2.2 to 2.6 of a DS (such as cellulose disuccinate, cellulose dipalmitate, cellulose dioctanoate and cellulose dicaprylate) and mixed cellulose ester (such as cellulose acetate valerate, cellulose acetate succinate, cellulose propionate succinate, cellulose acetate octanoate, cellulose valerate palmitate, cellulose acetate heptanoate, etc.). The semipermeable polymer is mentioned in U.S. Pat. No. 4,077, 407 and such a polymer is available by synthesizing according to a method mentioned in "Encyclopedia of Polymer Science and Technology", Volume 3, pages 325 to 354 (1964), Interscience Publishers, Inc., New York, N.Y. With regard to the compounding rate of the polymer used, there is no particular limitation so far as it is an amount where permeability for external liquids such as water and body fluids is high but permeability for tamsulosin, osmagent, osmopolymer, etc. is substantially impermeable although the amount is preferably 6 to 20 w/w % or, more preferably, 8 to 18 w/w % to the weight of the two-layered compressed core comprising the drug layer and the push layer.

The semipermeable polymer for the formation of semipermeable membrane further includes cellulose acetaldehyde dimethyl acetate, cellulose acetate ethyl carbamate, cellulose acetate methyl carbamate, cellulose dimethylaminoacetate, semipermeable polyurethane, semipermeable sulfonated polystyrene; or cross-linked selectively semipermeable polymer formed by co-precipitation from anion and cation being disclosed in U.S. Pat. Nos. 3,173,876, 3,276,586, 3,541,005, 3,541,006 and 3,546,142; semipermeable polymer, semipermeable polystyrene derivative, semipermeable poly(sodium styrenesulfonate) and semipermeable poly(vinylbenzyltrimethylammonium chloride) being disclosed in U.S. Pat. No. 3,133,132; and semipermeable polymer showing a liquid permeability of $10^{-5}$ to $10^{-2}$ (cc ml/cm hr atm) in terms of a hydrostatic pressure difference or an osmotic pressure difference per atmosphere upon permeating through a semipermeable wall. Such polymers are mentioned in U.S. Pat. Nos. 3,845,770, 3,916,899 and 4,160,020 and is also reported in "Handbook of Common Polymers" by Scott and Roff, 1971, CRC Press, Cleveland, Ohio.

The semipermeable membrane may contain a flux-regulating agent. The term "flux-regulating agent" used here stands for a substance which helps the adjustment of liquid permeability or liquid amount passing through the semipermeable membrane. Thus, a "flux-regulating agent" contains a substance having an action of increasing the flux (hereinafter, referred to as "flux-increasing agent") or a substance having an action of decreasing the flux (hereinafter, referred to as "flux-decreasing agent". The flux-increasing agent is substantially hydrophilic while the flux-decreasing agent is substantially hydrophobic. Examples of such a flux-increasing agent are polyhydric alcohol, polyalkylene glycol, polyalkylene diol and alkylene glycol polyester. Representative flux-increasing includes polyethylene glycol 300, 400, 600, 1500, 4000, 6000, etc.; low-molecular glycol such as polypropylene glycol, polybutylene glycol and polyamylene glycol; polyalkylene diol such as poly(1,3-propanediol), poly(1,4-butanediol), poly(1,6-hexanediol), etc.; fatty acid such as 1,3-butylene glycol, 1,4-pentamethylene glycol, 1,4-hexamethylene glycol, etc.; alkylene triol such as glycerol, 1,2,3-butanetriol, 1,2,4-hexanetriol, 1,3,6-hexanetriol, etc.; and ester such as ethylene glycol dipropionate, ethylene glycol butyrate, butylene glycol dipropionate, glycerol acetate ester, etc. Preferred flux-increasing agent includes propylene glycol bifunctional block copolymer polyoxyalkylene or derivatives thereof known as Pluronic (trade mark) (manufactured by BASF). Representative flux-decreasing agent includes alkyl- or alkoxy-substituted or alkyl- and alkoxy-substituted phthalate such as diethyl phthalate, dimethoxy ethyl phthalate and dimethyl phthalate, [di(2-ethylhexyl) phthalate], aryl phthalate such as triphenyl phthalate and butyl benzyl phthalate; insoluble salt such as calcium sulfate, barium sulfate, calcium phosphate, etc.; insoluble oxide such as titanium oxide; polymer in powder, particles, etc. such as polystyrene, polymethyl methacrylate, polycarbonate and polysulfone; ester such as citrate esterified with a long-chain alkyl group; and inactive and water-impermeable filler such as resin which is compatible with a material for formation of semipermeable member of a cellulose type.

Compounding amount of the "flux-regulating agent" contained in the semipermeable membrane is about 0.01 to about 20 w/w % or more.

Semipermeable membrane may contain a plasticizer of a phthalate type such as dibenzyl phthalate, dihexyl phthalate, butyl octyl phthalate, C6-11 straight-chain phthalate, di-isononyl phthalate, di-isodecyl phthalate, etc. in order to give plasticity, softness and spreading property to semipermeable membrane, in order not to make semipermeable membrane fragile or in order to give tear strength to semipermeable membrane. Examples of such a plasticizer are non-phthalate such as triacetin, dioctyl azelate, epoxidized tallate, triisooctyl trimellitate, triisononyl mellitate, sucrose acetate isobutyrate, epoxidized soybean oil, etc.

Compounding amount of the plasticizer contained in the semipermeable membrane ranges from about 0.01 to 20 w/w % or more.

The push layer used is in a state of contact layered alignment to a drug layer. In order to extrude tamsulosin or a pharmaceutically acceptable salt thereof from orifice of the preparation, the push layer contains an osmopolymer which is swollen upon absorption of aqueous liquid or body fluids. The term "osmopolymer" used here stands for a polymer which is highly swollen or expanded as a result of interaction with water or with aqueous biological fluids. Preferred osmopolymer as such is a hydrophilic polymer which is able to expand showing a volume increase of 2- to 50-fold. The osmopolymer may be either cross-linked or not cross-linked although, in a preferred embodiment, it is advantageous to be at least slightly cross-linked so as to form a polymer network structure which is enlarged to such an extent of being too large for coming out from the preparation. Although the compounding amount of the "osmopolymer" used depends upon the factors such as characteristic, content, etc. of the drug in the drug layer, there is no particular limitation therefor provided that it is an amount which is able to release the drug in the drug layer at desired release rate. It is however preferred to contain not less than 30 mg and, more preferably, not less than 50 mg. Compounding rate to the weight of the push layer is 40 to 80 w/w %.

The "osmopolymer" used contains a component selected from poly(alkylene oxide) having a number-average molecular weight of 1,000,000 to 15,000,000 represented by polyethylene oxide or poly(alkali carboxymethyl cellulose) having a number-average molecular weight of 500,000 to 3,500,000 (where alkali is sodium, potassium or lithium). There are further listed osmopolymer containing a hydrogel-forming polymer such as Carbopol (registered trade mark), acidic carboxyl polymer, acryl polymer cross-linked with polyallylsucrose which is known as carboxypolymethylene, a carboxyvinyl polymer having a molecular weight of 250,000 to 4,000,000; Cyanamer (registered trade mark) polyacrylamide; cross-linked water-swelling anhydrous indene maleic acid polymer; Good-rite (registered trade mark) polyacrylic acid having a molecular weight of 80,000 to 200,000; acrylate polymer polysaccharide comprising a fused glucose unit such as Aqua-Keeps (registered trade mark) and diester cross-linked polyglucan; etc. Polymers which form hydrogel are mentioned in U.S. Pat. Nos. 3,865,108, 4,002,173 and U.S. Pat. No. 4,207,893 and also reported in "Handbook of Common Polymers" by Scott and Roff, Chemical Rubber Co., Cleveland, Ohio.

With regard to the osmagent used here (which may also be called an osmotic solute or an osmotically effective agent), that may be contained in both layers of a drug layer containing tamsulosin or a pharmaceutically acceptable salt thereof and a push layer and there is no particular limitation therefor so far as it shows an osmotic gradient via a semipermeable membrane. With regard to such an osmagent, one or more member(s) selected from a group consisting of sodium chloride, potassium chloride, lithium chlorite, magnesium sulfate, magnesium chloride, potassium sulfate, sodium sulfate, lithium sulfate, potassium acidic phosphate, mannitol, glucose, lactose, sorbitol, inorganic salt, organic salt and carbohydrate may be listed. Compounding amount of the osmagent used is 15 to 40 w/w % to the weight of the push layer.

With regard to a solvent which is suitable for the manufacture of the constituting element for the preparation, water-soluble or inactive organic solvent which does not affect harmfully to the substances used in the system is listed. The solvent broadly covers a component selected from a group consisting of aqueous solvent, alcohol, ketone, ester, ether, aliphatic hydrocarbon, halogenated solvent, alicyclic, aromatic and heterocyclic solvent and a mixture thereof. Representative solvent includes acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride nitroethane, nitropropane tetrachloroethane, ethyl ether, isopropyl ether, cyclohexane, cyclooctane, benzene, toluene, naphtha, 1,4-dioxane, tetrahydrofuran, diglyme, water, an aqueous solvent containing inorganic salt such as sodium chloride and calcium chloride and a mixture thereof such as acetone and water, acetone and methanol, acetone and ethyl alcohol, methylene chloride and methanol and ethylene dichloride and methanol.

The drug layer used is constituted from a pharmaceutical composition comprising tamsulosin or a pharmaceutically acceptable salt thereof in a pharmacologically effective amount for therapy or prevention and a carrier for sustained-release pharmaceutical composition. Such a carrier for a sustained-release pharmaceutical composition may contain a hydrophilic polymer. Such a hydrophilic polymer provides an action of releasing tamsulosin or a pharmaceutically acceptable salt thereof at a certain rate. Such a polymer includes poly(alkylene oxide) with a number-average molecular weight of 100,000 to 750,000 such as poly(ethylene oxide), poly(methylene oxide), poly(butylene oxide) and poly(hexylene oxide); and poly(carboxymethyl cellulose) with a number-average molecular weight of 40,000 to 400,000 in which the representative ones are poly(alkali carboxymethyl cellulose), poly(sodium carboxymethyl cellulose), poly(potassium carboxymethyl cellulose) and poly(lithium carboxymethyl cellulose). The pharmaceutical composition may contain hydroxypropyl alkyl cellulose with a number-average molecular weight of 9,200 to 125,000 in which the representative ones are hydroxypropyl ethyl cellulose, hydroxypropyl methylcellulose, hydroxypropyl butyl cellulose and hydroxypropyl pentyl cellulose for improving the delivery characteristic of the preparation; and poly(vinylpyrrolidone) with a number-average molecular weight of 7,000 to 75,000 for improving the flow properties of the preparation. Among the polymers as such, the particularly preferred one is poly(ethylene oxide) with a number-average molecular weight of 100,000 to 300,000. Although compounding ratio of the hydrophilic polymer used is dependent upon the factors such as physico-chemical property, content, etc. of the drug contained therein, it is 40 to 90 w/w % to the weight of the drug layer.

If desired, a surface-active agent or a disintegrating agent may be compounded in the drug layer. With regard to the surface-active agent, that where an HLB value is about 10 to 25 such as polyethylene glycol 400 monostearate, polyoxyethylene 4 sorbitan monolaurate, polyoxyethylene 20 sorbitan monooleate, polyoxyethylene 20 sorbitan monopalmitate, polyoxyethylene 20 monolaurate, polyoxyethylene 40 stearate and sodium oleate may be listed. With regard to the disintegrating agent, that may be selected from starch, clay, cellulose, argine and gum and cross-linked starch, cellulose and polymer. Representatively, corn starch, potato starch, croscarmellose, crospovidone, sodium starch glycolate, Veegum HV, methyl cellulose, agar, bentonite, carboxymethyl cellulose, alginic acid, guar gum, etc. may be listed.

Pan coating may be used for the manufacture of a finished preparation except an exit orifice on the surface of the preparation for releasing the drug. In a pan coating system, a composition for forming a semipermeable membrane may be adhered (coated) by spraying a semipermeable membrane onto the surface of a two-layered compressed core being constituted from a push layer and a drug layer tumbling in a rotating pan. It is also possible to use for coating the above-mentioned compressed core with a semipermeable membrane according to a publicly known and common art for persons having a common knowledge in the said technical field. After the semipermeable membrane is coated, the semipermeable membrane is dried in a compulsorily aerating furnace or in a furnace where temperature and humidity are controlled whereupon the solvent(s) used for the coating may be removed from the preparation. The drying condition used here may be appropriately selected depending upon available device, environmental condition, solvent, coating agent, thickness of the coat, etc.

The sustained-release pharmaceutical composition may be manufactured by a known method per se. For example, the preparation may be manufactured by a wet granulation technique. With regard to the wet granulation technique, an organic solvent such as denatured anhydrous alcohol is used as a solution for the granulation and a drug and a carrier for the sustained-release pharmaceutical composition are blended. Other components may be dissolved in a part of the solution for granulation such as the above-mentioned solvent and a wet mixture, which is prepared separately, is gradually added to the drug mixture together with a continuous mixing in a mixer. After that, the solution for granulation is added until a wet mixture is formed. The wet block mixture is passed through a screen which is previously placed on an oven tray. Then the mixture is dried in a compulsory aeration furnace at the temperature of about 24° C. to 35° C. for about 18 to about 24 hours. After that, the dried particles are made uniform for their size. Then a lubricant such as magnesium stearate is added to the drug particles and the particles are placed in a finely-disintegrating jar and mixed for about 10 minutes using ajar mill. The composition is pressed into layers using, for example, a Manesty (registered trade mark) pressing machine or a Korsch LCT pressing machine. In a two-layered core, a drug-containing layer is pressed and a wet blend of a push layer composition similarly manufactured is pressed to the drug-containing layer. One or more exit orifice(s) is/are opened at the end of the drug layer of the preparation. In order to provide a finished preparation, a water-soluble overcoat (which may be either colored (such as an Opadry-colored coating) or transparent (such as an Opadry-clear) may be applied if necessary.

At least one exit orifice is formed in the sustained-release pharmaceutical preparation. The exit orifice releases the drug uniformly from the preparation in cooperation with a compressed core. The exit orifice may be installed either during the manufacture of the preparation or during the delivery of the drug by the preparation under the aqueous environment used. The term "exit orifice", "delivery orifice" or "drug delivery orifice" and other similar terms used here include terms selected from a group consisting of passage, opening, orifice and bore. The expression further includes an opening formed by polymer or substance which is eroded, dissolved or invaded from outer wall. The substance or the polymer may also include a pore-forming substance having an ability of removal of fluid selected from a group consisting of, for example, invading poly(glycolic acid) or poly(lactic acid); gelatinous filament; water-removing poly(vinyl alcohol); and an invading compound such as inorganic and organic salt, oxide and carbohydrate. Exit orifice(s) is/are formed by installing exit orifice(s) with small diameter(s) in such a size that one or more component(s) selected from a group consisting of sorbitol, lactose, fructose, glucose, mannose, galactose, talose, sodium chloride, potassium chloride, sodium citrate and mannitol is/are percolated so that control for a constant release of the drug is possible. The exit orifice may be in any of the shapes such as circle, rectangle, square, ellipse, etc. for a predetermined release of the drug from the preparation. In the preparation, one or more exit orifice(s) is/are formed in a predetermined interval or by having on one or more surface(s) of the preparation. With regard to the diameter of the exit orifice, there is no particular limitation provided that control of release of the drug is made possible in cooperation with the compressed core but, preferably, it is 0.3 mm to 0.6 mm. For the formation of the exit orifice, a hole making method passing through the semipermeable membrane including mechanical hole making and a laser hole making method may be used. An exit orifice as such and a device for the formation of an exit orifice as such is disclosed in U.S. Pat. No. 3,916,899 by Theeuwes and Higuchi and in U.S. Pat. No. 4,088,864 by Theeuwes, et al. and, in the present specification, all of the contents mentioned in those patents are incorporated.

(C) Gel Preparation Where a Plurality of Gums are Combined

The carrier for the sustained-release pharmaceutical composition used comprises a sustained-release excipient comprising hetero polysaccharide gum and homo polysaccharide which is able to form a cross-linkage with the hetero polysaccharide gum when exposed to an environmental fluid; inert diluent selected, for example, from monosaccharide, disaccharide, polyhydric alcohol and a mixture thereof; and a pharmaceutically-acceptable water-soluble cationic cross-linking agent for giving a sustained-releasing property of the drug at least for about 24 hours when the preparation is exposed to an environmental fluids. In the "environmental fluid", an aqueous solution used, for example, for an in vitro dissolution test may be included in addition to body fluid such as blood and gastric fluid.

As mentioned in U.S. Pat. Nos. 4,994,276, 5,128,143 and 5,135,757, it has been known that a hetero-dispersing excipient comprising a combination of homo polysaccharide and hetero polysaccharide showing synergism such as a combination of two or more polysaccharide gums has been higher viscosity than any of a single gum and results in a rapid hydration and that the such a gel is formed more rapidly and becomes harder.

The "hetero polysaccharide" used is defined as a water-soluble polysaccharide containing two or more sugar units. With regard to such a hetero polysaccharide, there is no particular limitation so far as it has branched-chain or spiral steric configuration and has an excellent water absorptive property and a high viscosity property. With regard to the hetero saccharide as such, xanthan gum and derivative thereof such as deacylated xanthan gum, carboxymethyl ether and propylene glycol ester are preferred. Advantageous ones are hetero polysaccharide having a high molecular weight (>106) and xanthan gum.

The "homo polysaccharide" used is defined as a single polysaccharide comprising one kind of monosaccharide. With regard to such a homo polysaccharide, there is no particular limitation so far as it is able to form a cross-linkage with a hetero polysaccharide. With regard to the homo polysaccharide as such, galactomannan gum (a polysaccharide comprising mannose and galactose only) is listed. Preferred one is locust bean gum where galactose is substituted with mannose in a relatively high rate.

With regard to a combination of "hetero polysaccharide" with "homo polysaccharide", a combination of xanthan gum with locust bean gum is particularly preferred. With regard to a compounding ratio of "hetero polysaccharide" with "homo polysaccharide", there is no particular limitation so far as it is an appropriate amount effective for obtaining desired gel strength. With regard to the ratio as such, the ratio of hetero polysaccharide gum to galactomannan gum ranges from about 3:1 to about 1:3 and, more preferably, about 1:1.

Homo polysaccharide is not limited to galactomannan gum and a sustained-release excipient comprises about 1 to about 99 w/w % of hetero polysaccharide gum and about 99 to 1 w/w % of homo polysaccharide gum. With regard to the compounding ratio of the gum, it is about 30 to about 60 w/w % or, preferably, about 35 to about 50 w/w % to the total weight of a sustained-release pharmaceutical composition.

The ratio of tamsulosin or a pharmaceutically acceptable salt thereof to gum usually ranges from about 1:1 to about 1:5 and, preferably, from about 1:1.5 to about 1:4.

With regard to a water-soluble cationic cross-linking agent used, there is no particular limitation so far as it is pharmaceutically acceptable and a monovalent or polyvalent metal cation. With regard to a linking agent as such, examples of the preferred one are various inorganic salts, e.g. those with alkali metal and/or alkaline metal, such as sulfate, chloride, borate, bromide, citrate, acetate and lactate. More specifically, examples of the linking agent are calcium sulfate, sodium chloride, potassium sulfate, sodium carbonate, lithium chloride, tripotassium phosphate, sodium borate, potassium bromide, potassium fluoride, sodium hydrogen carbonate, calcium chloride, magnesium chloride, sodium citrate, sodium acetate, calcium lactate, magnesium sulfate and sodium fluoride. With regard to the above-mentioned polyvalent metal cation, a divalent one is suitable. With regard to a salt, calcium sulfate or sodium chloride is suitable.

Applying amount of the water-soluble cationic cross-linking agent, it is preferably about 1 to about 20 w/w % to the total weight of a sustained-release pharmaceutical composition. Most preferably, the linking agent is about 10 w/w % to the total weight of the pharmaceutical composition.

With regard to an inert diluent, there is no particular limitation so far as it is pharmaceutically acceptable. With regard to a diluent as such, sugar including mono- and di-saccharide, polyhydric alcohol, cellulose derivative and/or a mixture of the above-mentioned ones may be exemplified. To be more specific, sucrose, dextrose, lactose, finely crystalline cellulose, hydroxypropyl methylcellulose, hydroxypropyl cellulose, carboxymethyl cellulose, fructose, xylitol, sorbitol and a mixture thereof may be exemplified. Among them, it is preferred to use a soluble diluent for the preparation such as lactose, dextrose, sucrose or a mixture thereof.

With regard to the above-mentioned sustained-release pharmaceutical composition, it may be manufactured as a pharmaceutically acceptable solid pharmaceutical dosage form for oral use such as tablet. With regard to such a sustained-release pharmaceutical composition, (1) hetero polysaccharide gum and homo polysaccharide which is able to subject the hetero polysaccharide gum to a cross-linking when exposed to environmental fluids are dried and mixed in a desired ratio together with a pharmaceutically acceptable inert diluent, (2) the mixture is subjected to a wet granulation, (3) the granules are dried, (4) the dried granules are pulverized to give a sustained-release excipient with a desired particle size, the resulting sustained-release excipient is (5) granulated together with tamsulosin or a pharmaceutically acceptable salt thereof, (6) the resulting granules are dried, then (7) an inert excipient (such as a lubricant) is added thereto and the mixture is then, for example, (8) molded with compression to give tablets. In another embodiment, a mixture of a sustained-release excipient and tamsulosin or a pharmaceutically acceptable salt thereof is granulated together with a solution of a hydrophobic substance in an amount which is sufficient for retarding its hydration without destroying the gum. After that, an inert excipient (such as a lubricant) is further added thereto and the mixture is, for example, made into tablets by a compression molding.

Wet granulation is that predetermined amounts of hetero polysaccharide gum, homo polysaccharide gum, cationic cross-linking agent and inert diluent are homogeneously mixed, then a moisturizing agent such as water, propylene glycol, glycerol or alcohol is added, the prepared wet agglomerates are dried and the dried agglomerates are pulverized using a conventional device whereupon granules having a predetermined particle size are prepared.

With regard to the lubricant, stearic acid, magnesium stearate, calcium stearate, sodium stearylfumarate, etc. may be listed and sodium stearylfumarate (Edward Mendell Co., Inc.; trade name: PruvR) is particularly preferred. With regard to the amount of the lubricant, about 0.5 to 3 w/w % to the total weight of the sustained-release pharmaceutical composition is applied. With regard to a method for applying the hydrophobic substance with a sustained-release excipient, a method where further granulation is carried out together with the above-mentioned granules using a solution of a hydrophobic substance is dissolved and/or dispersed in an organic solvent may be exemplified.

With regard to a hydrophobic substance, ethyl cellulose, acrylic and/or methacrylic acid polymer or copolymer, hydrogenated vegetable oil, zein and pharmaceutically acceptable hydrophobic cellulose substance such as alkyl cellulose may be exemplified. Adding amount of such a hydrophobic substance to the total weight of the sustained-release pharmaceutical composition is preferably about 1 to about 20 w/w %, more preferably about 3 to about 12 w/w % and, still more preferably, about 5 to about 10 w/w %.

An example of the best combination of the components is that xanthan gum as a "hetero polysaccharide" and locust bean gum as a "homo polysaccharide" in a compounding ratio of about 1:1 are applied in amount of about 35 to about 50 w/w % to the total weight of a sustained-release pharmaceutical composition and then not more than about 10 w/w % of calcium sulfate as a "water-soluble cationic cross-linking agent", about 35 w/w % of dextrose as an "inert diluent" and about 5 to about 10 w/w % of ethyl cellulose as a "hydrophobic substance" are applied therewith.

(D) Multi-Layered Tablet Comprising a Geometrically Aligned Drug Layer and Release-Controlling Layer(s)

A carrier for a sustained release pharmaceutical composition used comprises a drug-containing layer and release-controlling layer(s) and comprises the following constitution.

a) the first layer (layer 1) which is manufactured by compressing of a mixture or granules containing 5 to 90 w/w % (preferably 10 to 85 w/w %) of a water-soluble polymer in the layer and having a property of being swollen by contact to environmental fluids;

b) the second layer (layer 2) comprising a water-soluble polymer and other auxiliary substances and containing tamsulosin or a pharmaceutically acceptable salt thereof (preferably, a hydrochloride) which is adjacent to the first layer, has a suitable properties of compressibility and is designed to release a physiologically active substance within a predetermined time; and, if necessary c) the third layer (layer 3) being adhered to the layer 2 which comprises a water-soluble polymer which is generally gelled and/or swollen followed by freely disintegrating and has a function of controlling the release of tamsulosin or a pharmaceutically acceptable salt thereof (preferably, a hydrochloride) from the layer 2. "Environmental fluids" includes an aqueous solution such as that used for a dissolution test in addition to body fluids such as blood, gastric fluids and intestinal fluids.

As mentioned in U.S. Pat. Nos. 4,839,177 and 5,422,123, the above-mentioned sustained-release pharmaceutical composition is characterized in that the layer 2 containing the drug is sandwiched by the layer 1 and the layer 3 where drug is not contained or is optionally contained whereby a releasing rate of the drug from the pharmaceutical preparation is controlled. In addition, as mentioned in U.S. Pat. Nos. 5,780,057 and 6,149,940, it has been known that, in the above-mentioned sustained-release pharmaceutical composition, at least one of the layer 1 and the layer 3 is quickly expanded when contacted to body fluids and then the layer 2 is expanded or, in other words, volume of the pharmaceutical composition significantly increases whereupon there is a function that the pharmaceutical composition remains in the stomach for a longer period and most of the contained active ingredient is released and absorbed at the upper area of the gastrointestinal tract with a controlled manner.

The layer 1 and the layer 3 may have the same composition and the same functional characteristic or they may have different composition and different characteristic. When the layer 1 and the layer 3 have the same functional characteristic and composition, their amounts and thickness sandwiching the layer 2 may be changed. At least one of the layer 1 and the layer 3 acts as a barrier for release of the active ingredient or, in other words, it is impermeable wherefrom tamsulosin or a salt thereof (preferably, a hydrochloride) contained in the layer 2 is not released or diffused and at least one of the layers has a characteristic that it quickly expands or, in other words, its volume quickly increases. The layer 3 contains the drug optionally so that it is possible to supplementarily give the release of a drug which is different from the layer 2.

Amount of tamsulosin or a pharmaceutically acceptable salt thereof (preferably, a hydrochloride) is as mentioned already.

With regard to the water-soluble polymer used in the layer 1, the layer 3 and the layer 2, there is no particular limitation so far as it is pharmaceutically acceptable and has a biocompatibility. Such a water-soluble polymer is gradually dissolved and/or gradually gelled in an aqueous liquid and/or may be gelled quickly or in a different rate and then optionally disintegrated. Specific examples of such a water-soluble polymer are hydroxymethyl cellulose, hydroxyethyl cellulose, hydroxypropyl methyl cellulose with a molecular weight of 1,000 to 4,000,000, hydroxypropyl cellulose with a molecular weight of 2,000 to 2,000,000, carboxyvinyl polymer, chitosan, mannan, galactomannan, xanthan, carrageenan, amylase, alginic acid or salt or derivative thereof, pectin, acrylate, methacrylate, acrylic/methacrylic acid copolymer, polyacid anhydride, polyamino acid, poly(methyl vinyl ether/maleic acid anhydride) polymer, polyvinyl alcohol, glucan, scleroglucan, carboxymethyl cellulose and derivative thereof, ethyl cellulose, methyl cellulose and common water-soluble cellulose derivative. Preferred one is hydroxypropyl methylcellulose with a molecular weight of 3,000 to 2,000,000. Applying amount of the layer 1 and the layer 3 to the weight thereof is usually 5 to 90 w/w %, preferably 10 to 85 w/w % and, still more preferably, 20 to 80 w/w %. Applying amount of the water-soluble polymer in the layer 2 to the weight thereof is usually 5 to 90 w/w % and, preferably, 10 to 85 w/w %.

In order to quickly increase the volume of the pharmaceutical preparation containing the above-mentioned water-soluble polymer during the preparation of the layer 1 and the layer 3, it is possible to use a water-soluble excipient which promotes the degree of wet of the layers. With regard to such a water-soluble excipient, it is preferred to select from a group of the so-called super-disintegrating excipients such as cross-linked polyvinylpyrrolidone, low-molecular or medium-molecular hydroxypropyl cellulose and hydroxypropyl methylcellulose, cross-linked carboxymethyl cellulose sodium, carboxymethyl starch and salt thereof, divinylbenzene/potassium methacrylate copolymer, etc. Compounding amount of the excipient is not more than 1 to 90 w/w % and, preferably, 5 to 50 w/w % of the layer. If necessary, surfactant (anionic, cationic and nonionic ones) may be used for improving the wetting so that environmental fluids and tablets are made more compatible whereby the pharmaceutical composition, particularly gel-forming layer, can be quickly gelled. Examples of such a substance are sodium laurylsulfate, sodium ricinolate, sodium tetradeculsulfonate, sodium dioctylsulfosuccinate, cetomagrogol, poloxamer, glycerol monostearate, polysolvate, sorbitan monolaurate, lecithins and any other pharmaceutically acceptable surfactants. If necessary, it is also possible to use other substance which modifies hydration. Such a substance is selected from hydrophilic diluents such as mannitol, lactose, starch derived from various things, sorbitol, xylitol, microcrystalline cellulose and/or a substance which generally promotes the permeation of water or an aqueous liquid into a pharmaceutical composition; or a hydrophobic diluent such as ethyl cellulose, glycerol monostearate, palmitate, hydrogenated or non-hydrogenated vegetable oil (e.g., hydrogenated castor oil, wax, monoglyceride, diglyceride and triglyceride), etc. which retard the permeation of water or an aqueous liquid into the pharmaceutical preparation. Preferably, it is desirable to select ethyl cellulose or hydrogenated vegetable oil as a hydrophobic diluent. Amount of the hydrophobic diluents in the layer 1 and the layer 3 is usually 1 to 60 w/w %, preferably 5 to 40 w/w % and, more preferably, 10 to 30 w/w % to the weight thereof.

The sustained-release pharmaceutical preparation may contain a lubricant such as magnesium stearate, talc, stearic acid, glycerol monostearate, polyoxyethylene glycol having a molecular weight of 400 to 7,000,000, hydrogenated castor oil, glycerol behenate, monoglyceride, diglyceride, triglyceride, etc.; fluidizing agents such as colloidal silica or any other silica; binders; buffers; absorbing agents; and pharmaceutically acceptable other additives.

Tablet comprising the sustained-release pharmaceutical composition is manufactured by a method, for example, where powder and/or particles are/is mixed by a manufacturing technique known per se followed by subjecting to compression. A pharmaceutical composition comprising two or three layers (such as tablet) may be manufactured by a known tableting method known per se. The tablet of the present invention may be manufactured using, for example, a rotary press which is able to manufacture "multi-layered" tablets. Compressing pressure for the manufacture of tablets is usually 7 to 50 KN (or kilonewtons). In the manufacture of tablets in a small scale, it is also possible that powder and/or particles for each are/is prepared using mortar and pestle and tablets comprising two or three layers are manufactured using an oil press tableting machine. Thickness of each layer of the tablet may vary depending upon the amount of an active ingredient although it is within a range of preferably 0.2 to 8 mm and, more preferably, 1 to 4 mm. In the pharmaceutical composition (such as tablet) of the present invention, a coating layer with a polymer material may be applied to the pharmaceutical composition with the object of, for example, protection of tablet or retardation of initial release of an active ingredient which is released from the pharmaceutical composition. The coating may have solubility in an acidic solution or have permeability so that, after a predetermined time, the tablet releases the active ingredient. Such a coating may be applied by a known method per se using an organic or aqueous solution.

The pharmaceutical composition (such as tablet) quickly increases its volume by contacting with liquids and/or gastrointestinal fluids. An increase in volume as such may be decided and limited in a single layer or several layers in the tablet. Such a pharmaceutical composition (such as tablet) is characterized in that, after 2 hours, volume of at least one layer increases to an extent of 1.5- or, preferably, at least 3-fold of the initial volume. The pharmaceutical composition may be in a form of a tablet, small tablets or a gelatin capsule comprising small tablets. It is also possible that at least two small tablets are combined in the same pharmaceutical composition. They may, for example, be packed in a wafer capsule or gelatin capsule. When a pharmaceutical composition comprises small tablets, each of them may have different or same composition.

(E) Gastroretentive Dosage Form Using Swelling Polymers

The carrier used for a sustained-release pharmaceutical composition comprises a high-molecular water-soluble polymer which is swollen upon absorption of water. Such a polymer may be used either solely or in a combined manner.

The carrier used for a sustained-release pharmaceutical composition is mentioned, for example, in U.S. Pat. Nos. 6,340,475, 5,972,389, 5,582,837 and 5,007,790 and, in the present specification, all of the contents mentioned in the above-mentioned specifications are incorporated.

With regard to the "high-molecular water-soluble polymer which is swollen upon absorption of water", there is no particular limitation so far as it is pharmaceutically acceptable, swollen without limitation in terms of size upon absorption of water and able to release the drug in a sustained manner. The polymer as such is preferably a polymer with a weight-average molecular weight of not less than about 4,500,000, more preferably a polymer with a weight-average molecular weight of about 4,500,000 to about 10,000,000 and, particularly preferably, a polymer with a weight-average molecular weight of about 5,000,000 to about 8,000,000.

With regard to the polymer as such, cellulose polymer and derivative thereof, polysaccharide and derivative thereof, polyalkylene oxide and cross-linked polyacrylic acid and derivative thereof are listed. Here, the term "cellulose" stands for a linear polymer of anhydroglucose. Preferred cellulose polymer is an alkyl-substituted cellulose polymer which is soluble in the gastrointestinal tract. Preferred alkyl-substituted cellulose derivative is that which is substituted with a C1-3 alkyl group each. Examples of such a polymer are methylcellulose, hydroxymethyl cellulose, hydroxyethyl cellulose, hydroxypropyl cellulose, hydroxypropyl methylcellulose and carboxymethyl cellulose. Preferred viscosity includes the case where viscosity of a 2% aqueous solution at 20° C. is within a range of about 100 to about 110,000 cps. Other type includes the case where viscosity of a 1% aqueous solution at 20° C. is within a range of about 1,000 to about 4,000 cps. Particularly preferred alkyl-substituted cellulose is hydroxyethyl cellulose and hydroxypropyl methylcellulose. Preferred hydroxyethyl cellulose at present is Natrasol (registered trade mark) 250 HX NF.

As to the particularly preferred one as such a polymer, a polyalkylene oxide derivative is listed and more preferred polyalkylene oxide is polyethylene oxide which stands for a linear polymer of unsubstituted ethylene oxide. Preferred polyethylene oxide has a weight-average molecular weight within a range of about 900,000 to about 8,000,000. Preferred viscosity range includes the case where viscosity of a 2% aqueous solution at 20° C. is within a range of about 50 to about 2,000,000 cps. Preferred polyethylene oxide at present is Polyox (registered trade mark) and Grade WSR Coagulant and Grade WSR 303 may be listed.

Additional examples of such a polymer are both natural and modified (semi-synthetic) polysaccharide gums such as dextran, xanthan gum, gellan gum, welan gum and rhamsan gum in which xanthan gum is preferred. In cross-linked polyacrylic acid having the highest usefulness, its property is the same as the above-mentioned one to alkyl-substituted cellulose and polyalkylene oxide polymer. Preferred cross-linked polyacrylic acid is that, in a form of a 1% aqueous solution at 25° C., its viscosity is within a range of about 4,000 to about 40,000 cps. Preferred examples at present are Carbopol (registered trade mark) NF grade 971 P, 974 P and 934 P or Water lock (registered trade mark) which is a copolymer of starch, acrylate and acrylamide.

Ratio by weight of tamsulosin or a pharmaceutically acceptable salt thereof to the "high-molecular water-soluble polymer swollen upon absorption of water" is within a range of about 15:85 to about 80:20, preferably about 30:70 to about 80:20 and, more preferably, within a range of about 30:70 to about 70:30.

A sustained-release pharmaceutical composition is manufactured as pharmaceutically acceptable oral solid dosage form such as tablets, particles or particles which in able to be enclosed in tablet or capsule. Preferred dosage form at present is that, for example, two or three drug-containing polymer particles (pellets) are enclosed in a No. 0 gelatin capsule. Preferred size of a pellet for enclosing two pellets in a No. 0 gelatin capsule is a diameter of 6.6 mm to 6.7 mm (or, more commonly, 6.5 mm to 7 mm) and a length of 9.5 mm or 10.25 mm (or, more commonly, 9 mm to 12 mm). Preferred size of a pellet for enclosing three pellets in a No. 0 gelatin capsule is a diameter of 6.6 mm and a length of 7 mm. Preferred size of a pellet for enclosing two pellets in a No. 00 gelatin capsule is a diameter of 7.5 mm and a length of 11.5 mm. Preferred size of a pellet for enclosing three pellets in a No. 00 gelatin capsule is a diameter of 7.5 mm and a length of 7.5 mm. Preferred other dosage form at present is a tablet having a length of 18 mm to 22 mm, a width of 6.5 mm to 7.8 mm and a height of 6.2 mm to 7.5 mm and a preferred combination of length, width and height of a tablet is 20 mm length, 6.7 mm width and 6.4 mm height. They are mere exemplifications and the shape and the size can be changed to a considerable extent.

A granular drug/polymer mixture or a polymer matrix in which a drug is impregnated may be manufactured by various mixing, pulverizing and manufacturing techniques by methods which were in public. For example, a direct compression or an injection or compression molding using appropriate punch and die may be listed. During the compression molding, a lubricant may be added. With regard to the lubricant, stearic acid, magnesium stearate, calcium stearate, sodium stearylfumarate, etc. may be listed and magnesium stearate is particularly preferred. Compounding amount of the lubricant to the total weight of the sustained-release composition is 0.25 to 3 w/w % and, preferably, less than 1 w/w %. With regard to other lubricant, hydrogenated vegetable oil and triglyceride of hydrogenated and purified stearic acid and palmitic acid are preferred and compounding amount thereof to the weight of the sustained-release pharmaceutical composition is about 1 to 5 w/w % or, most preferably, about 2 w/w %.

With regard to the optimum combination of the above-mentioned components, compounding of polyethylene oxide with a weight-average molecular weight within a range of about 2,000,000 to about 7,000,000 as "a high-molecular water-soluble polymer swelling upon absorption of water" in an amount of about 90 to about 97 w/w % to the total weight of a sustained-release pharmaceutical composition and magnesium stearate as a "lubricant" in an amount of less than about 2 w/w % to total weight of a sustained-release pharmaceutical composition is listed. With regard to a combination of, for example, two kinds of water-soluble polymers, compounding of polyethylene oxide with a weight-average molecular weight within a range of about 900,000 to about 7,000,000 and hydroxypropyl methyl cellulose with a viscosity of about 3 to about 10,000 cps as a 2% aqueous solution in a compounding ratio of about 1:1 in an amount of about 48 w/w % each is listed.

(F) Matrix Preparation Using Water-Soluble Polymers

A matrix tablet comprising water-soluble polymers is a sustained-released pharmaceutical preparation in which the drug is uniformly dispersed in water-soluble polymer substrates such as hydroxypropyl methylcellulose.

The matrix preparation is mentioned, for example, in International Laid-Open Pamphlet No. 93/16686 and all of the contents mentioned in the above specification are incorporated in the present specification.

When hydroxypropyl methylcellulose, which is a water-soluble polymer, is hydrated when contacted with water and forms a hydrogel layer on the surface of a tablet. When the gel layer containing the drug formed on the surface of the tablet is gradually dissolved and eroded, the drug is released. The present tablet has a characteristic that the drug is released with a sustained manner by repetition of contact with water, formation of gel layer containing the drug and dissolution and erosion of the gel layer.

The pharmaceutical sustained-release preparation has a characteristic that sustained-release excipients comprising water-soluble polymers are uniformly dispersed together with other inert diluents and a physiologically active ingredient. With regard to the water-soluble substrates, there is no particular limitation so far as it is gradually gelled and/or eroded and/or dissolved and/or disintegrated when exposed to environmental fluids. Examples of such a water-soluble substrate are hydroxypropyl methylcellulose, hydroxymethyl cellulose, hydroxyethyl cellulose with a molecular weight of 1,000 to 4,000,000, hydroxypropyl cellulose with a molecular weight of 2,000 to 2,000,000, carboxyvinyl polymer, chitosan, mannan, galactomann, xanthan, carrageenan, amylase, alginic acid and a salt and a derivative thereof, pectin, acrylate, methacrylate, acrylic/methacrylic acid copolymer, poly acid anhydride, polyamino acid, poly(methyl vinyl ether/maleic acid anhydride) polymer, polyvinyl alcohol, glucan, scleroglucan, carboxymethyl cellulose and derivative thereof, ethyl cellulose, methylcellulose and a common water-soluble cellulose derivative. Preferred one is hydroxypropyl methylcellulose with a molecular weight of 1,000 to 2,000,000 or carboxyvinyl polymer where a 0.5% aqueous solution (25° C.) is 3,000 to 45,000 cps. More preferred one is hydroxypropyl methylcellulose having a molecular weight of 10,000 to 1,000,000 or carboxyvinyl polymer where viscosity of a 0.5% aqueous solution (25° C.) is 4,000 to 40,000 cps. Amount of the water-soluble polymer per preparation unit is 5 to 95 w/w %, preferably 10 to 90 w/w % and, more preferably, 30 to 85 w/w %.

Various kinds of excipients for pharmaceuticals are appropriately used for the pharmaceutical composition whereupon a pharmaceutical preparation is manufactured. With regard to such an excipient for pharmaceuticals, there is no particular limitation so far as it is pharmaceutically acceptable and is used as an additive to pharmaceuticals. For example, diluents, binders, disintegrating agents, acidic agents, foaming agents, artificial sweeteners, perfumes, lubricants, coloring agents, etc. may be used. A diluent is selected from a group of the following substances: mannitol, lactose, starch derived from various sources, sorbitol, xylitol, microcrystalline cellulose and/or a water-soluble diluent which generally promotes the permeation of water or an aqueous liquid into the pharmaceutical preparation. Examples of a binder are hydroxypropyl methylcellulose, hydroxypropyl cellulose, polyvinyl alcohol, methylcellulose and gum acacia. Examples of a disintegrating agent are corn starch, starch, calcium carmellose, sodium carmellose and lowly-substituted hydroxypropyl cellulose. Examples of an acidic agent are citric acid, tartaric acid and malic acid. Examples of a foaming agent are sodium bicarbonate, etc. Examples of an artificial sweetener are saccharin sodium, dipotassium glycyrrhizin, aspartame, stevia and thaumatin. Examples of a perfume are lemon, lemon lime, orange and menthol. Examples a lubricant are magnesium stearate, calcium stearate, sucrose fatty acid ester, polyethylene glycol, talc and stearic acid. With regard to such a pharmaceutical excipient, one excipient may be used or two or more excipients may be used jointly.

A tablet comprising the pharmaceutical composition can be manufactured by a known method per se. Such a tablet can be manufactured by a method for tableting which is very commonly used and is known among persons skilled in the field. Usually, the tablet compressing force for the operation is within a range of 3 to 20 KN (or kilonewtons). When tablets are manufactured in a small scale, it is also possible that, according to a method which will be mentioned in more detail in Examples, each powder and/or granule is prepared using mortar and pestle followed by manufacturing tablets using an oil press tableting machine.

With regard to a method for the administration of tamsulosin or a pharmaceutically acceptable salt thereof of the present invention which reduces adverse reactions accompanied by therapy or prevention of an $\alpha$ receptor blocking action, that can be carried out by a method mentioned in the above Detailed Description of the Invention concerning a sustained-release pharmaceutical composition.

EXAMPLES

The present invention will be further illustrated by way of the following Examples, Test Examples and Experimental Examples although the present is not limited to those examples.

Example A (Sustained-Release Hydrogel-Forming Preparation)

Example A-1

PEG 6000 (3.84 parts) was dissolved in 10.56 parts of water using a magnetic stirrer. Under stirring with a magnetic stirrer, 1.6 parts of tamsulosin hydrochloride previously pulverized by a hammer mill (Sample Mill AP-S, using a 1-mm screen, manufactured by Hosokawa Micron) were suspended (partially dissolved) to prepare a spray liquid. PEG 6000 (56.16 parts) and 300 parts of PEO (product name: Polyox™ WSR-303, Dow Chemical) were charged in a fluidized bed granulator (Flow Coater, manufactured by Furointo) and the above spray liquid was sprayed under the conditions of an inlet air temperature of 25° C., a spraying rate of 5 g/minute and a spraying/drying cycle of 20 seconds/40 seconds to prepare particles. After that, the particles were dried at an inlet air temperature of 40° C. for 30 minutes. Magnesium stearate (1.8 parts) was added to 361.6 parts of the dried particles followed by mixing and the mixture was subjected to a compression to make the tablets with an average weight of 181.7 mg using a rotary tableting machine (HT P-22, manufactured by Hata Tekkosho). The pestles of 8.5 mm diameter were used and 400 kgf/pestle of the compressing pressure was applied to give a sustained-release preparation of the present invention (tablets).

Example A-2

PEG 6000 (3.84 parts) was dissolved in 10.56 parts of water using a magnetic stirrer. Under stirring with a magnetic stirrer, 1.6 parts of tamsulosin hydrochloride previously pulverized by a hammer mill (Sample Mill AP-S, using a 1-mm screen, manufactured by Hosokawa Micron) were suspended (partially dissolved) to prepare a spray liquid. Then, 76.16 parts of PEG 6000 and 400 parts of PEO (product name: polyox™ WSR-303, Dow Chemical) were charged in a fluidized bed granulator (Flow Coater, manufactured by Furointo) and the above spray liquid was sprayed under the conditions of an inlet air temperature of 25° C., a spraying rate of 5 g/minute and a spraying/drying cycle of 20 seconds/40 seconds to prepare particles. After that, the particles were dried at an inlet air temperature of 40° C. for 30 minutes. Magnesium stearate (2.4 parts) was added to 481.6 parts of the dried particles followed by mixing and the mixture was subjected to a compression to make the tablets with an average weight of 242 mg using a rotary tableting machine (HT P-22, manufactured by Hata Tekkosho). The pestles of 9 mm diameter were used and 400 kgf/pestle of the compressing pressure was applied to give a sustained-release preparation of the present invention (tablets).

Example A-3

PEG 6000 (3.84 parts) was dissolved in 10.56 parts of water using a magnetic stirrer. Under stirring with a magnetic stirrer, 1.6 parts of tamsulosin hydrochloride previously pulverized by a hammer mill (Sample Mill AP-S, using a 1-mm screen, manufactured by Hosokawa Micron) were suspended (partially dissolved) to prepare a spray liquid. Then, 96.16 parts of PEG 6000 and 500 parts of PEO (product name: Polyox™ WSR-303, Dow Chemical) were charged in a fluidized bed granulator (Flow Coater, manufactured by Furointo) and the above spray liquid was sprayed under the conditions of an inlet air temperature of 25° C., a spraying rate of 5 g/minute and a spraying/drying cycle of 20 seconds/40 seconds to prepare particles. After that, the particles were dried at an inlet air temperature of 40° C. for 30 minutes. Magnesium stearate (3 parts) was added to 601.6 parts of the dried particles followed by mixing and the mixture was subjected to a compression to make the tablets with an average weight of 302.3 mg using a rotary tableting machine (HT P-22, manufactured by Hata Tekkosho). The pestles of 9.5 mm diameter were used and 400 kgf/pestle of the compressing pressure was applied to give a sustained-release preparation of the present invention (tablets).

Example A-4

PEG 6000 (3.84 parts) was dissolved in 10.56 parts of water using a magnetic stirrer. Under stirring with a magnetic stirrer, 1.0 part of tamsulosin hydrochloride previously pulverized by a hammer mill (Sample Mill AP-S, using a 1-mm screen, manufactured by Hosokawa Micron) was suspended (partially dissolved) to prepare a spray liquid. Then, 76.16 parts of PEG 6000 and 400 parts of PEO (product name: Polyox™ WSR-303, Dow Chemical) were charged in a fluidized bed granulator (Flow Coater, manufactured by Furointo) and the above spray liquid was sprayed under the conditions of an inlet air temperature of 25° C., a spraying rate of 5 g/minute and a spraying/drying cycle of 20 seconds/40 seconds to prepare particles. After that, the particles were dried at an inlet air temperature of 40° C. for 30 minutes. Magnesium stearate (2.4 parts) was added to 481.0 parts of the dried particles followed by mixing and the mixture was subjected to a compression to make the tablets with an average weight of 241.7 mg using a rotary tableting machine (HT P-22, manufactured by Hata Tekkosho). The pestles of 9 mm diameter were used and 400 kgf/pestle of the compressing pressure was applied to give a sustained-release preparation of the present invention (tablets).

Example A-5

PEG 6000 (3.84 parts) was dissolved in 10.56 parts of water using a magnetic stirrer. Under stirring with a magnetic stirrer, 2.0 parts of tamsulosin hydrochloride previously pulverized by a hammer mill (Sample Mill AP-S, using a 1-mm screen, manufactured by Hosokawa Micron) were suspended (partially dissolved) to prepare a spray liquid. Then, 76.16 parts of PEG 6000 and 400 parts of PEO (product name: Polyox™ WSR-303, Dow Chemical) were charged in a fluidized bed granulator (Flow Coater, manufactured by Furointo) and the above spray liquid was sprayed under the conditions of an inlet air temperature of 25° C., a spraying rate of 5 g/minute and a spraying/drying cycle of 20 seconds/40 seconds to prepare particles. After that, the particles were dried at an inlet air temperature of 40° C. for 30 minutes. Magnesium stearate (2.4 parts) was added to 482.0 parts of the dried particles followed by mixing and the mixture was subjected to a compression to make the tablets with an average weight of 242.2 mg using a rotary tableting machine (HT P-22, manufactured by Hata Tekkosho). The pestles of 9 mm diameter were used and 400 kgf/pestle of the compressing pressure was applied to give a sustained-release preparation of the present invention (tablets).

Example A-6

PEG 6000 (3.84 parts) was dissolved in 10.56 parts of water using a magnetic stirrer. Under stirring with a magnetic stirrer, 0.5 part of tamsulosin hydrochloride previously pulverized by a hammer mill (Sample Mill AP-S, using a 1-mm screen, manufactured by Hosokawa Micron) were suspended (partially dissolved) to prepare a spray liquid. Then, 76.16 parts of PEG 6000 and 400 parts of PEO (product name: Polyox™ WSR-303, Dow Chemical) were charged in a fluidized bed granulator (Flow Coater, manufactured by Furointo) and the above spray liquid was sprayed under the conditions of an inlet air temperature of 25° C., a spraying rate of 5 g/minute and a spraying/drying cycle of 20 seconds/40 seconds to prepare particles. After that, the particles were dried at an inlet air temperature of 40° C. for 30 minutes. Magnesium stearate (2.4 parts) was added to 480.5 parts of the dried particles followed by mixing and the mixture was subjected to make the tablets with an average weight of 241.5 mg using a rotary tableting machine (HT P-22, manufactured by Hata Tekkosho). The pestles of 9 mm diameter were used and 400 kgf/pestle of the compressing pressure was applied to give a sustained-release preparation of the present invention (tablets).

Test Example A1 (Dissolution Test)

Drug-releasing characteristic of each of the preparations of Examples A-1 to A-5 was evaluated by the Method II, Dissolution Test, Japanese Pharmacopoeia (paddle method). Distilled water (900 mL) was used as a test medium and, without a sinker, the test was conducted at a paddle rotation speed of 200 rpm. Sampling was done for each time and tamsulosin hydrochloride in the sampling solution was quantified by means of an HPLC equipped with a UV spectrophotometer (225 nm). The result is shown in Table 1.

TABLE 1

| Examples | A-1 | A-2 | A-3 | A-4 | A-5 |
|---|---|---|---|---|---|
| Tamsulosin released at 3 h (%) | 25 | 23 | 20 | 24 | 25 |
| Tamsulosin released at 7 h (%) | 67 | 55 | 47 | 56 | 58 |
| Tamsulosin released at 12 h (%) | 95 | 89 | 78 | 89 | 90 |

(Results and Considerations)

When polyethylene oxide was used as a hydrogel-forming substrate and PEG was used as a hydrophilic base, a sustained drug release was noted for tamsulosin hydrochloride. The drug release could be controlled by loading amounts of polyethylene oxide and PEG.

As shown in Experimental Examples which will be mentioned later, in clinical investigations using Example A-2 (or A-4, 5, 6), the result was that efficacy was equivalent or even better than the current preparation and, with regard to the adverse reactions, it was reduced as compared with the current preparation. Accordingly, in preparations showing similar pharmacokinetic parameters obtained in oral administration in Example A-2, it is expected that efficacy at the same dose is equivalent or even better as compared with the current preparation and that the occurrence of adverse events is reduced. It is also expected to increase the dose or to eliminate the restriction on ingestion of meals.

Example B (An Osmotic Pump Type Preparation)

Step 1: Manufacture of Mixed Powder Constituting a Drug Layer Containing an Active Ingredient A mixed powder containing 0.80 mg of tamsulosin hydrochloride and having the following compositions was prepared and used for the manufacture of two-layered compressed core.

| | |
|---|---|
| Tamsulosin hydrochloride | 0.80 mg |
| Lactose | 7.20 mg |
| Polyethylene oxide (Polyox ™ WSR N80) | 100 mg |
| Hydroxypropyl methylcellulose (HPMC 2910) | 6 mg |
| Magnesium stearate | 1.00 mg |
| Total | 115.00 mg |

The drug and various additives were weighed according to the above-mentioned compositions and well mixed using a mortar and a pestle until uniform mixture was obtained.

Step 2: Manufacture of a Pushing Layer

A mixed powder having the following compositions was prepared and used for the manufacture of two-layered compressed core.

| | |
|---|---|
| Polyethylene oxide (Polyox ™ WSR Coagulant) | 60 mg |
| NaCl | 30 mg |
| Hydroxypropyl methylcellulose (HPMC 2910) | 4 mg |
| Red ferric oxide | 1 mg |
| Magnesium stearate | 0.5 mg |
| Total | 95.5 mg |

The various additives were weighed according to the above-mentioned compositions and well mixed using a mortar and a pestle until uniform mixture was obtained.

Step 3: Manufacture of a Two-Layered Compressed Core Comprising a Drug Layer and a Pushing Layer The two-layered compressed core was prepared using an oil press tableting machine. A pestle of 8.0 mm diameter×9.6 R was used. A mixed powder for pushing layer is charged in a mortar, then a mixed powder for drug layer is layered thereon and compression was carried out to give a two-layered compressed core containing 0.8 mg of tamsulosin hydrochloride.

Step 4: Preparation of Semipermeable Membrane and Membrane Coating

PEG 400 and cellulose acetate (94:6 (w/w %)) were dissolved in a mixed solvent of dichloromethane and methanol (9:1 (w/w %)). This coating solution contains about 4% of solid in use. This coating solution was subjected to a spray coating onto the above-manufactured two-layered compressed core using a coating machine of an aeration type (High Coater HCT-30, manufactured by Furointo Sankyo) until the amount of the coating component becomes 10 w/w % of the weight of the two-layered compressed core.

Step 5: Holing

The tablet coated with a semipermeable membrane as such was holed on the side of the drug layer using an injection needle (27G) of 0.4 mm diameter. Preparations of Examples B-2 to B-13 mentioned in Table 2 and Table 3 were manufactured in the same manner as above mentioned.

TABLE 2

| | Examples | | | | | |
|---|---|---|---|---|---|---|
| | B-2 | B-3 | B-4 | B-5 | B-6 | B-7 |
| Drug Layer | | | | | | |
| Tamsulosin hydrochloride | 0.8 | 0.8 | 0.8 | 0.8 | 0.8 | 0.8 |
| Lactose | 7.2 | 7.2 | 7.2 | 7.2 | 7.2 | 7.2 |
| Polyox ® WSR N10 | — | — | — | 20 | — | — |
| Polyox ® WSR N80 | 100 | 100 | 100 | 80 | 20 | 100 |
| Polyox ® WSR N750 | — | — | — | — | 80 | — |
| HPMC 2910 | 6 | 6 | 6 | 6 | 6 | 6 |
| Magnesium stearate | 1 | 1 | 1 | 1 | 1 | 1 |
| Total | 115 | 115 | 115 | 115 | 115 | 115 |
| Push Layer | | | | | | |
| Polyox ® WSR Coagulant | 60 | 60 | 60 | 60 | 60 | 90 |
| NaCl | 30 | 30 | 30 | 30 | 30 | 30 |
| HPMC 2910 | 4 | 4 | 4 | 4 | 4 | 6 |

TABLE 2-continued

|  | Examples | | | | | |
| --- | --- | --- | --- | --- | --- | --- |
|  | B-2 | B-3 | B-4 | B-5 | B-6 | B-7 |
| Ferric sesquioxide | 1 | 1 | 1 | 1 | 1 | 1 |
| Magnesium stearate | 0.5 | 0.5 | 0.5 | 0.5 | 0.5 | 0.5 |
| Total | 95.5 | 95.5 | 95.5 | 95.5 | 95.5 | 127.5 |
| Grand Total | 210.5 | 210.5 | 210.5 | 210.5 | 210.5 | 242.5 |
| Diameter | 8 | 8 | 8 | 8 | 8 | 8 |
| Semipermeable Membrane | | | | | | |
| Cellulose acetate | 19.787 | 19.787 | 19.787 | 19.787 | 19.787 | 22.795 |
| PEG 400 | 1.263 | 1.263 | 1.263 | 1.263 | 1.263 | 1.455 |
| Orifice diameter (mm) and | 0.33 | 0.5 | 0.4 | 0.4 | 0.4 | 0.4 |
| Number(s) | one | one | two | one | one | one |

TABLE 3

|  | Examples | | | | | |
| --- | --- | --- | --- | --- | --- | --- |
|  | B-8 | B-9 | B-10 | B-11 | B-12 | B-13 |
| Drug Layer | | | | | | |
| Tamsulosin hydrochloride | 0.8 | 0.8 | 0.8 | 0.8 | 0.8 | 0.8 |
| Lactose | 7.2 | 7.2 | 7.2 | 7.2 | 7.2 | 7.2 |
| Polyox ® WSR N10 | — | — | — | — | — | — |
| Polyox ® WSR N80 | 100 | 100 | 100 | 100 | 100 | 100 |
| Polyox ® WSR N750 | — | — | — | — | — | — |
| HPMC 2910 | 6 | 6 | 6 | 6 | 6 | 6 |
| Magnesium stearate | 1 | 1 | 1 | 1 | 1 | 1 |
| Total | 115 | 115 | 115 | 115 | 115 | 115 |
| Push Layer | | | | | | |
| Polyox ® WSR Coagulant | 120 | 60 | 60 | 60 | 60 | 60 |
| NaCl | 30 | 30 | 30 | 30 | 30 | 30 |
| HPMC 2910 | 4 | 4 | 4 | 4 | 4 | 4 |
| Ferric sesquioxide | 1 | 1 | 1 | 1 | 1 | 1 |
| Magnesium stearate | 0.5 | 0.5 | 0.5 | 0.5 | 0.5 | 0.5 |
| Total | 158.5 | 95.5 | 95.5 | 95.5 | 95.5 | 95.5 |
| Grand Total | 273.5 | 210.5 | 210.5 | 210.5 | 210.5 | 210.5 |
| Diameter | 8 | 8 | 8 | 8 | 8 | 8 |
| Semipermeable Membrane | | | | | | |
| Cellulose acetate | 25.709 | 14.642 | 23.74 | 27.10 | 32.054 | 34.825 |
| PEG 4000 | 1.641 | 0.934 | 1.516 | 1.730 | 2.046 | 2.222 |
| Orifice diameter (mm) | 0.4 | 0.4 | 0.4 | 0.4 | 0.4 | 0.4 |

Test Example B (Dissolution Test)

Test Example B-1

Releasing property of preparations of Examples B-1 to B-13 was evaluated according to a method of Test Example A and the result is shown in Table 4. In addition, lag time until initiation of drug release was determined from the drug release profile and the value where the lag time was 0 hour wherefrom releasing rate after initiation of drug release is shown in Table 5.

|  | Example B- | | | | | | | | | | | | |
| --- | --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 | 13 |
| Tamsulosin released at 3 h (%) | 12 | 8 | 9 | 9 | 7 | 4 | 8 | 1 | 26 | 6 | 2 | 0 | 0 |
| Tamsulosin released at 7 h (%) | 45 | 39 | 41 | 41 | 38 | 43 | 42 | 35 | 71 | 38 | 30 | 23 | 19 |
| Tamsulosin released at 12 h (%) | 77 | 70 | 77 | 75 | 70 | 80 | 79 | 71 | 90 | 72 | 56 | 47 | 41 |

TABLE 5

| | Example B- | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Tamsulosin released at 3 h (%) | 22 | 21 | 23 | 22 | 21 | 25 | 24 | 23 | 33 | 22 | 18 | 16 | 14 |
| Tamsulosin released at 7 h (%) | 50 | 48 | 53 | 51 | 49 | 59 | 55 | 54 | 78 | 51 | 42 | 36 | 32 |
| Tamsulosin released at 12 h (%) | 86 | 82 | 91 | 88 | 84 | 100 | 94 | 93 | 100 | 88 | 72 | 63 | 55 |

(Results and Considerations)

In the preparations of an osmotic pump type, any of them showed a lag time (time zone where no drug release is noted) of about 2 hours for initiating the release of the drug. After initiation of drug release, a sustained drug-releasing profile was shown where the drug release rate at 3 hours after lag time was 14% to 33%, at 7 hours thereof was 32% to 78% and at 12 hours thereof was 55% or more in all preparations and, therefore, they were sustained-release pharmaceutical compositions with similar drug release profiles obtained in Example A-2. Accordingly, it is considered that the similar pharmacokinetic parameters are obtained as those of A-2 preparation in case of the administration at the same dose, therefore, it is expected that, as compared with the current preparation, the efficacy is equivalent or better and occurrence of adverse events is reduced. It is also expected to increase the dose or to eliminate the restriction on ingestion of meals.

Example C (Gel Preparation Where a Plurality of Gums are Combined)

Example C-1

The powder comprising the following various composition units was prepared by weighing 5 parts of locust bean gum (Sansho; San-Ace M175), 5 parts of xanthan gum (Nitta Gelatin, VS 900), 7 parts of dextrose (Wako Pure Chemical) and 1 part of calcium sulfate (Kanto Kagaku) followed by well mixing using a mortar and a pestle until being uniformity was achieved. Into the prepared mixed powder were gradually dropped 2 mL (1 mL×2 times) of pure water followed by well stirring and mixing using a pestle to granulate. The prepared granules were sieved using a 16-mesh sieve (0.59 □m) and dried at the constant temperature of 40° C. for 12 hours to give granulated powder A.

To the granulated powder A were added tamsulosin hydrochloride and lactose and a 10% solution of ethyl cellulose dissolved in methanol (100 mg/mL) was gradually dropped thereinto followed by well stirring and mixing using a pestle to give a granulated powder B. The granulated powder B was dried at the constant temperature of 40° C. for 12 hours. The dried granulated powder B was charged in a mortar and subjected to compression by an oil press tableting machine using a pestle of 8.0 mm diameter×8.0 R with tablet compressing pressure of 1,000 kg/pestle to manufacture tablets having an average weight of 202.00 mg.

| Tamsulosin hydrochloride | 0.80 mg |
|---|---|
| Lactose | 7.20 mg |
| Locust bean gum (Sansho, San-Ace M175) | 50.00 mg |
| Xanthan gum (Nitta Gellatin, VS 900) | 50.00 mg |
| Dextrose | 70.00 mg |
| Calcium sulfate | 10.00 mg |
| Ethyl cellulose | 14.00 mg |
| Total | 202.00 mg |

Example C-2

To the granulated powder A were added tamsulosin hydrochloride and lactose and a 10% solution of ethyl cellulose dissolved in methanol (100 mg/mL) was gradually dropped thereinto followed by well stirring and mixing using a pestle to give a granulated powder C. The granulated powder C was dried at the constant temperature of 40° C. for 12 hours. The dried granulated powder C was charged in a mortar and subjected to compression by an oil press tableting machine using a pestle of 8.0 mm diameter×8.0 R with compressing pressure of 1,000 kg/pestle to manufacture tablets having an average weight of 396.00 mg.

| Tamsulosin hydrochloride | 0.80 mg |
|---|---|
| Lactose | 7.20 mg |
| Locust bean gum (Sansho, San-Ace M175) | 100.00 mg |
| Xanthan gum (Nitta Gellatin, VS 900) | 100.00 mg |
| Dextrose | 140.00 mg |
| Calcium sulfate | 20.00 mg |
| Ethyl cellulose | 28.00 mg |
| Total | 396.00 mg |

Example C-3

To the granulated powder A were added tamsulosin hydrochloride and lactose and a 10% solution of ethyl cellulose dissolved in methanol (100 mg/mL) was gradually dropped thereinto followed by well stirring and mixing using a pestle to give a granulated powder D. The granulated powder D was dried at the constant temperature of 40° C. for 12 hours. The dried granulated powder D was charged in a mortar and subjected to compression by an oil tableting machine using a pestle of 8.0 mm diameter×8.0 R with compressing pressure of 1,000 kg/pestle to manufacture tablets having an average weight of 590.00 mg.

| Tamsulosin hydrochloride | 0.80 mg |
|---|---|
| Lactose | 7.20 mg |
| Locust bean gum (Sansho, San-Ace M175) | 150.00 mg |
| Xanthan gum (Nitta Gellatin, VS 900) | 150.00 mg |
| Dextrose | 210.00 mg |
| Calcium sulfate | 30.00 mg |
| Ethyl cellulose | 42.00 mg |
| Total | 590.00 mg |

Example C (Dissolution Test)

Test Example C-1

According to the method of Test Example A, releasing property of the preparations of Examples C1 to C3 was evaluated and the result is shown in Table 6.
(Results and Considerations)

TABLE 6

| Examples | C-1 | C-2 | C-3 |
|---|---|---|---|
| Tamsulosin released at 3 h (%) | 45 | 33 | 32 |
| Tamsulosin released at 7 h (%) | 88 | 70 | 54 |
| Tamsulosin released at 12 h (%) | 85 | 72 | 68 |

As a result of using gels where a plurality of gums were combined, a sustained drug-released was achieved. Tamsulosin release from these preparations can be controlled by loading amount of locust bean gum and xanthan gum. Drug release after 7 hours from the initiation of dissolution, was between about 54% and about 88%. Accordingly, it is considered that the similar pharmacokinetic parameters are obtained as those of A-2 preparation in case of the administration at the same dose, therefore, it is expected that, as compared with the current preparation, the efficacy is equivalent or better and occurrence of adverse events is reduced. It is also expected to increase the dose or to eliminate the restriction on ingestion of meals.

Example D (Multi-Layered Tablet Preparation Comprising Geometrically-Aligned Drug Layer and Release-Controlling Layers)

Example D-1

Manufacture of Three-Layered Tablet Containing Tamsulosin Hydrochloride

Step 1A: Manufacture of a Mixed Powder Constituting the Layer 2 Containing an Active Ingredient A mixed powder containing 0.80 mg of tamsulosin hydrochloride and comprising the following composition units was manufactured and used for the manufacture of the layer 2 which is an intermediate layer for the three-layered tablet.

| | |
|---|---|
| Tamsulosin hydrochloride | 0.80 mg |
| Lactose | 7.20 mg |
| Mannitol | 10.00 mg |
| Hydroxypropyl methylcellulose (HPMC 90SH-15000) | 10.00 mg |
| Polyvinylpyrrolidone | 3.20 mg |
| Microcrystalline cellulose | 66.55 mg |
| Magnesium stearate | 1.00 mg |
| Colloidal silica | 1.25 mg |
| Total | 100.00 mg |

The powder comprising the above composition units was prepared by weighing necessary amounts of an active ingredient, mannitol, microcrystalline cellulose, hydroxypropyl methylcellulose (HPMC 90SH-15000), polyvinylpyrrolidone, magnesium stearate and colloidal silica followed by mixing using a mortar and a pestle until uniform mixture was obtained.

Step 1B: Manufacture of Particles Constituting the Layer 1 (The Layer 1 Containing No Drug) Used for Control Drug Particles comprising the following composition units were manufactured and used for the manufacture of the layer 1 which is the uppermost layer for the three-layered tablet.

| | |
|---|---|
| HPMC (90SH-15000) | 80.96 mg |
| Hydrogenated castor oil | 13.71 mg |
| Yellow ferric oxide | 0.25 mg |
| Ethyl cellulose | 5.08 mg |
| Total | 100.00 mg |

A manufacturing method comprises that necessary amounts of hydroxypropyl methylcellulose (HPMC 90SH-15000), hydrogenated castor oil and yellow ferric oxide were weighed and well mixed using a mortar and a pestle until uniform mixture was obtained. The particles were prepared in such a manner that the homogeneous powder mixture was wetted with a 10 w/v% alcoholic solution of ethyl cellulose base, the homogeneously wetted agglomerates were dried at 40° C. and passed through a sieve.

Step 1C: Manufacture of Particles Constituting the Layer 3 (The Layer 3 Containing No Drug) Used for Control of Drug Release Particles comprising the following composition units were manufactured and used for the manufacture of the layer 3 which is the lowermost layer for the three-layered tablet.

| | |
|---|---|
| HPMC (90SH-15000) | 121.45 mg |
| Hydrogenated castor oil | 20.56 mg |
| Yellow ferric oxide | 0.38 mg |
| Ethyl cellulose | 7.61 mg |
| Total | 150.00 mg |

Particles used for the layer 3 which is the lowermost layer of the three-layered tablet are manufactured according to the method mentioned in Example D-1 (Step 1B).

Step 1D: Manufacture of Three-Layered Tablet (Compression Molding)

A three-layered tablet was prepared by an oil press tableting machine. A pestle of 8.0 mm diameter×9.6 R is used, and 1,000 kg/pestle of the compressing pressure were applied. The particles for the layer 3 mentioned in the item 1C were charged in a mortar and lightly tapped to make the upper surface flat. A mixed powder containing an active ingredient of the layer 2 mentioned in the item 1A was filled thereon and lightly tapped to make the upper surface flat. Further, the particles of the layer 1 mentioned in the item 1B was charged in the mortar thereon and subjected to a compression to manufacture three-layered tablets with an average weight of 350.00 mg and 0.80 mg of tamsulosin hydrochloride. The layer 1 and the layer 3 may be charged in the mortar in a reversed order followed by subjecting to a compressing.

Examples D-2 to D-13

Manufacture of Three-Layered Tablets Containing Tamsulosin Hydrochloride

Step 2A: Manufacture of Mixed Powder Constituting the Layer 2 Containing an Active Ingredient A mixed powder used for the manufacture of the layer 2 which is a middle layer of the three-layered tablet having 0.80 mg of tamsulosin hydrochloride is manufactured according to the method mentioned in Example D-1 (Step 1A). Each of the preparations of Examples D-2 to D-13 is shown in Table 7 and Table 8.

TABLE 7

| | Examples | | | | | |
|---|---|---|---|---|---|---|
| | D-2 | D-3 | D-4 | D-5 | D-6 | D-7 |
| Tamsulosin hydrochloride | 0.80 | 0.80 | 0.80 | 0.80 | 0.80 | 0.80 |
| Lactose | 7.20 | 7.20 | 7.20 | 7.20 | 7.20 | 7.20 |
| Mannitol | 10.00 | 10.00 | 10.00 | 10.00 | 10.00 | 10.00 |
| HPMC (90SH-4000) | — | — | — | — | — | — |
| HPMC (90SH-15000) | 10.00 | 10.00 | 10.00 | 10.00 | 10.00 | 10.00 |
| HPMC (90SH-100000) | — | — | — | — | — | — |
| PVP (K 30) | 3.20 | 3.20 | 3.20 | 3.20 | 3.20 | 3.20 |
| Microcrystalline cellulose | 66.55 | 66.55 | 66.55 | 66.55 | 66.55 | 66.55 |
| Magnesium stearate | 1.00 | 1.00 | 1.00 | 1.00 | 1.00 | 1.00 |
| Colloidal silica | 1.25 | 1.25 | 1.25 | 1.25 | 1.25 | 1.25 |
| Total (mg) | 100.00 | 100.00 | 100.00 | 100.00 | 100.00 | 100.00 |

TABLE 8

| | Examples | | | | | |
|---|---|---|---|---|---|---|
| | D-8 | D-9 | D-10 | D-11 | D-12 | D-13 |
| Tamsulosin hydrochloride | 0.80 | 0.80 | 0.80 | 0.80 | 0.80 | 0.80 |
| Lactose | 7.20 | 7.20 | 7.20 | 7.20 | 7.20 | 7.20 |
| Mannitol | 10.00 | 10.00 | 10.00 | 10.00 | 10.00 | 10.00 |
| HPMC (90SH-4000) | — | 10.00 | — | — | — | — |
| HPMC (90SH-15000) | 10.00 | 10.00 | — | 30.00 | 75.00 | 60.00 |
| HPMC (90SH-100000) | — | — | 10.00 | — | — | — |
| PVP (K 30) | 3.20 | 3.20 | 3.20 | 3.20 | 3.20 | 3.20 |
| Microcrystalline cellulose | 66.55 | 68.80 | 68.80 | 48.80 | 3.80 | 18.80 |
| Magnesium stearate | 1.00 | — | — | — | — | — |
| Colloidal silica | 1.25 | — | — | — | — | — |
| Total (mg) | 100.00 | 100.00 | 100.00 | 100.00 | 100.00 | 100.00 |

Step 2B: Manufacture of Particles Constituting the Layer 1 (The Layer 1 Containing No Drug) Used for Control of Drug Release Particles used for the manufacture of the layer 1 which is a layer for control of release of the drug is manufactured according to a method mentioned in Example D-1 (Step 1B). Each of the preparations of Examples D-2 to D-13 is shown in Table 9 and Table 10.

TABLE 9

| | Examples | | | | | |
|---|---|---|---|---|---|---|
| | D-2 | D-3 | D-4 | D-5 | D-6 | D-7 |
| HPMC (90SH-4000) | — | — | 80.96 | — | 40.48 | — |
| HPMC (90SH-15000) | 94.67 | 86.04 | — | — | 40.48 | 40.48 |
| HPMC (90SH-30000) | — | — | — | — | — | — |
| HPMC (90SH-100000) | — | — | — | 80.96 | — | — |
| Hydrogenated castor oil | — | 13.71 | 13.71 | 13.71 | 13.71 | 6.85 |
| Yellow ferric oxide | 0.25 | 0.25 | 0.25 | 0.25 | 0.25 | 0.13 |
| Ethyl cellulose | 5.08 | — | 5.08 | 5.08 | 5.08 | 2.54 |
| Total (mg) | 100.00 | 100.00 | 100.00 | 100.00 | 100.00 | 50.00 |

TABLE 10

| | Examples | | | | | |
|---|---|---|---|---|---|---|
| | D-8 | D-9 | D-10 | D-11 | D-12 | D-13 |
| HPMC (90SH-4000) | — | — | — | — | — | — |
| HPMC (90SH-15000) | 121.45 | 80.96 | 80.96 | 80.96 | 80.96 | — |
| HPMC (90SH-30000) | — | — | — | — | — | 60.72 |
| HPMC (90SH-100000) | — | — | — | — | — | — |
| Hydrogenated castor oil | 20.56 | 13.71 | 13.71 | 13.71 | 13.71 | 10.28 |
| Yellow ferric oxide | 0.38 | 0.25 | 0.25 | 0.25 | 0.25 | 0.19 |
| Ethyl cellulose | 7.61 | 5.08 | 5.08 | 5.08 | 5.08 | 3.81 |
| Total (mg) | 100.00 | 100.00 | 100.00 | 100.00 | 100.00 | 75.00 |

Step 2C: Manufacture of Particles Constituting the Layer 3 (The Layer 3 Containing No Drug) Used for Control of Drug Release Particles used for the manufacture of the layer 3 which is a layer for control of release of the drug is manufactured according to a method mentioned in Example D-1 (Step 1B). Each of the preparations of Examples D-2 to D-13 is shown in Table 9 and Table 10.

TABLE 11

| | Examples | | | | | |
|---|---|---|---|---|---|---|
| | D-2 | D-3 | D-4 | D-5 | D-6 | D-7 |
| HPMC (90SH-4000) | — | — | 121.45 | — | — | — |
| HPMC (90SH-15000) | 121.45 | 129.06 | — | — | 121.45 | 40.48 |
| HPMC (90SH-30000) | — | — | — | — | — | — |
| HPMC (90SH-100000) | — | — | — | 121.45 | — | — |
| Hydrogenated castor oil | 20.56 | 20.56 | 20.56 | 20.56 | 20.56 | 6.85 |
| Yellow ferric oxide | 0.38 | 0.38 | 0.38 | 0.38 | 0.38 | 0.13 |
| Ethyl cellulose | 7.61 | — | 7.61 | 7.61 | 7.61 | 2.54 |
| Total (mg) | 150.00 | 150.00 | 150.00 | 150.00 | 150.00 | 50.00 |

TABLE 12

| | Examples | | | | | |
|---|---|---|---|---|---|---|
| | D-8 | D-9 | D-10 | D-11 | D-12 | D-13 |
| HPMC (90SH-4000) | — | — | — | — | — | — |
| HPMC (90SH-15000) | 121.45 | 121.45 | 121.45 | 121.45 | 121.45 | — |
| HPMC (90SH-30000) | — | — | — | — | — | 60.72 |
| HPMC (90SH-100000) | — | — | — | — | — | — |
| Hydrogenated castor oil | 20.56 | 20.56 | 20.56 | 20.56 | 20.56 | 10.28 |
| Yellow ferric oxide | 0.38 | 0.38 | 0.38 | 0.38 | 0.38 | 0.19 |
| Ethyl cellulose | 7.61 | 7.61 | 7.61 | 7.61 | 7.61 | 3.81 |
| Total (mg) | 150.00 | 150.00 | 150.00 | 150.00 | 150.00 | 75.00 |

Step 2D: Manufacture of Three-Layered Tablet (Compression Molding)

A three-layered tablet containing 0.80 mg of tamsulosin hydrochloride is manufactured according to the method mentioned in Example D-1 (Step 1D)

Example D-14

Manufacture of Three-Layered Tablet Containing Tamsulosin Hydrochloride

Step 3A: Manufacture of a Mixed Powder Constituting the Layer 2 Containing an Active Ingredient A mixed powder containing 1.20 mg of tamsulosin hydrochloride and being used for the manufacture of the layer 2 which is a middle layer for the three-layered tablet is manufactured by the method mentioned in Example D-1 (Step 1A).

| | |
|---|---|
| Tamsulosin hydrochloride | 1.20 mg |
| Lactose | 10.80 mg |
| Mannitol | 15.00 mg |
| HPMC (90SH-15000) | 15.00 mg |
| Polyvinylpyrrolidone | 4.80 mg |
| Microcrystalline cellulose | 99.83 mg |
| Magnesium stearate | 1.50 mg |
| Colloidal silica | 1.87 mg |
| Total | 150.00 mg |

Step 3B: Manufacture of Particles Constituting the Layer 1 (The Layer 1 Containing No Drug) Used for Control of Drug Release The particles used for the manufacture of the layer 1 comprising the following composition units and being a layer for controlling the release of the drug are manufactured by the method mentioned in Example D-1 (Step 1B).

| | |
|---|---|
| HPMC (90SH-15000) | 80.96 mg |
| Hydrogenated castor oil | 13.71 mg |
| Yellow ferric oxide | 0.25 mg |
| Ethyl cellulose | 5.08 mg |
| Total | 100.00 mg |

Step 3C: Manufacture of Particles Constituting the Layer 3 (The Layer 3 Containing No Drug) Used for Control of Drug Release The particles used for the manufacture of the layer 3 comprising the following composition units and being a layer for controlling the release of the drug are manufactured by the method mentioned in Example D-1 (Step 1B).

| | |
|---|---|
| HPMC (90SH-15000) | 121.45 mg |
| Hydrogenated castor oil | 20.56 mg |
| Yellow ferric oxide | 0.38 mg |
| Ethyl cellulose | 7.61 mg |
| Total | 150.00 mg |

Step 3D: Manufacture of a Three-Layered Tablet (Compression Molding)

A three-layered tablet with an average weight of 400.00 mg and containing 1.20 mg of tamsulosin hydrochloride is manufactured according to the method mentioned in Example D-1 (Step 1D).

Example D-15

Manufacture of Three-Layered Tablet Containing Tamsulosin Hydrochloride

Step 4A: Manufacture of a Mixed Powder Constituting the Layer 2 Containing an Active Ingredient A mixed powder containing 1.60 mg of tamsulosin hydrochloride and being used for the manufacture of the layer 2 which is a middle layer for the three-layered tablet is manufactured by the method mentioned in Example D-1 (Step 1A).

| | |
|---|---|
| Tamsulosin hydrochloride | 1.60 mg |
| Lactose | 14.40 mg |
| Mannitol | 20.00 mg |
| HPMC (90SH-15000) | 20.00 mg |
| Polyvinylpyrrolidone | 6.40 mg |
| Microcrystalline cellulose | 133.10 mg |
| Magnesium stearate | 2.00 mg |
| Colloidal silica | 2.50 mg |
| Total | 200.00 mg |

Step 4B: Manufacture of Particles Constituting the Layer 1 (The Layer 1 Containing No Drug) Used for Control of Drug Release The particles used for the manufacture of the layer 1 comprising the following composition units and being a layer for controlling the release of the drug are manufactured by the method mentioned in Example D-1 (Step 1B).

| | |
|---|---|
| HPMC (90SH-15000) | 80.96 mg |
| Hydrogenated castor oil | 13.71 mg |
| Yellow ferric oxide | 0.25 mg |
| Ethyl cellulose | 5.08 mg |
| Total | 100.00 mg |

Step 4C: Manufacture of Particles Constituting the Layer 3 (The Layer 3 Containing No Drug) Used for Control of Drug Release The particles used for the manufacture of the layer 3 comprising the following composition units and being a layer for controlling the release of the drug are manufactured by a method mentioned in Example D-1 (Step 1B).

| | |
|---|---|
| HPMC (90SH-15000) | 121.45 mg |
| Hydrogenated castor oil | 20.56 mg |
| Yellow ferric oxide | 0.38 mg |
| Ethyl cellulose | 7.61 mg |
| Total | 150.00 mg |

Step 4D: Manufacture of a Three-Layered Tablet (Compression Molding)

A three-layered tablet with an average weight of 450.00 mg and containing 1.60 mg of tamsulosin hydrochloride is manufactured according to the method mentioned in Example D-1 (Step 1D).

Examples D-16 to C-17

Manufacture of Three-Layered Tablet Containing Tamsulosin Hydrochloride

Step 5A: Manufacture of a Mixed Powder Constituting the Layer 2 Containing an Active Ingredient A mixed powder containing 0.80 mg of tamsulosin hydrochloride and being used for the manufacture of the layer 2 which is a middle layer for the three-layered tablet is manufactured by the method mentioned in Example D-1 (Step 1A).

| | |
|---|---|
| Tamsulosin hydrochloride | 0.80 mg |
| Lactose | 7.20 mg |
| Mannitol | 10.00 mg |
| HPMC (90SH-15000) | 10.00 mg |

-continued

| | |
|---|---|
| Polyvinylpyrrolidone | 3.20 mg |
| Microcrystalline cellulose | 66.55 mg |
| Magnesium stearate | 1.00 mg |
| Colloidal silica | 1.25 mg |
| Total | 100.00 mg |

Step 5B: Manufacture of Particles Constituting the Layer 1 (The Layer 1 Containing No Drug) Used for Control of Drug Release The particles used for the manufacture of the layer 1 comprising the following composition units and being a layer for controlling the release of the drug are manufactured by the method mentioned in Example D-1 (Step 1B).

| | |
|---|---|
| HPMC (90SH-4000) | 20.24 mg |
| HPMC (90SH-15000) | 20.24 mg |
| Hydrogenated castor oil | 6.85 mg |
| Yellow ferric oxide | 0.13 mg |
| Ethyl cellulose | 2.54 mg |
| Total | 50.00 mg |

Step 5C: Manufacture of Particles Constituting the Layer 3 (The Layer 3 Containing No Drug) Used for Control of Drug Release The particles used for the manufacture of the layer 3 comprising the following composition units and being a layer for controlling the release of the drug are manufactured by the method mentioned in Example D-1 (Step 1B).

| | |
|---|---|
| HPMC (90SH-15000) | 121.45 mg |
| Hydrogenated castor oil | 20.56 mg |
| Yellow ferric oxide | 0.38 mg |
| Ethyl cellulose | 7.61 mg |
| Total | 150.00 mg |

Step 5D: Manufacture of a Three-Layered Tablet (Compression Molding)

A three-layered tablet is manufactured by an oil press tableting machine. In Example D-16, a pestle of 7.0 mm diameter×8.4 R is used, while in Example 17, a pestle of 9.5 mm diameter×11.4 R is used and, in both, 1,000 kg/pestle of the tableting pressure was applied. The particles of the layer 3 mentioned in the item of 5C are filled in a mortar and lightly tapped so that the upper surface becomes flat. A mixed powder containing an active ingredient of the layer 2 mentioned in the item 5A is filled thereon and lightly tapped to make the upper surface flat. Further, the particles of the layer 1 mentioned in the item 5B is charged thereon in the mortar and subjected to a compression to manufacture a three-layered tablet with an average weight of 300.00 mg and 0.80 mg of tamsulosin hydrochloride.

Example D-18

Manufacture of Three-Layered Tablet Containing Tansulosin Hydrochloride

Step 6A: Manufacture of a Mixed Powder Constituting the Layer 2 Containing an Active Ingredient A mixed powder containing 0.80 mg of tamsulosin hydrochloride and being used for the manufacture of the layer 2 which is a middle layer for the three-layered tablet is manufactured by the method mentioned in Example D-1 (Step 1A).

| | |
|---|---|
| Tamsulosin hydrochloride | 0.80 mg |
| Lactose | 7.20 mg |
| Mannitol | 10.00 mg |
| HPMC (90SH-15000) | 10.00 mg |
| Polyvinylpyrrolidone | 3.20 mg |
| Microcrystalline cellulose | 66.55 mg |
| Magnesium stearate | 1.00 mg |
| Colloidal silica | 1.25 mg |
| Total | 100.00 mg |

Step 6B: Manufacture of Particles Constituting the Layer 1 (The Layer 1 Containing No Drug) Used for Control of Drug Release The particles used for the manufacture of the layer 1 comprising the following composition units and being a layer for controlling the release of the drug are manufactured by the method mentioned in Example D-1 (Step 1B).

| | |
|---|---|
| HPMC (90SH-15000) | 80.96 mg |
| Hydrogenated castor oil | 13.71 mg |
| Yellow ferric oxide | 0.25 mg |
| Ethyl cellulose | 5.08 mg |
| Total | 100.00 mg |

Step 6C: Manufacture of Particles Constituting the Layer 3 (The Layer 3 Containing No Drug) Used for Control of Drug Release The particles used for the manufacture of the layer 3 comprising the following composition units and being a layer for controlling the release of the drug are manufactured by the method mentioned in Example D-1 (Step 1B).

| | |
|---|---|
| HPMC (90SH-15000) | 121.45 mg |
| Hydrogenated castor oil | 20.56 mg |
| Yellow ferric oxide | 0.38 mg |
| Ethyl cellulose | 7.61 mg |
| Total | 150.00 mg |

Step 6D: Manufacture of a Three-Layered Tablet (Compression Molding)

A three-layered tablet with a diameter of 8.0 mm is manufactured by an oil press tableting machine and 1,000 kg/pestle of the tableting pressure was applied. The particles of the layer 3 mentioned in the item of 6C are filled in a mortar and lightly tapped so that the upper surface becomes flat and, after that, it is lightly pushed by a convex pestle in the same diameter. A mixed powder containing an active ingredient of the layer 2 mentioned in the item 6A is filled thereon and lightly tapped with a pestle of 8.0 mm diameter×9.6 R. Further, the particles of the layer 1 mentioned in the item 6B is charged thereon in the mortar and subjected to a compression using a pestle of 8.0 mm diameter×9.6 R to manufacture a three-layered tablet with an average weight of 350.00 mg and 0.80 mg of tamsulosin hydrochloride. The layer 1 and the layer 3 may be charged in the mortar in a reversed order followed by subjecting to a compressing.

Example D-19

Manufacture of Two-Layered Tablet containing Tamsulosin Hydrochloride

Step 7A: Manufacture of a Mixed Powder Constituting the Layer Containing an Active Ingredient A mixed powder used for the manufacture of the layer containing 0.80 mg of tamsulosin hydrochloride is manufactured by the method mentioned in Example D-1 (Step 1A).

| | |
|---|---|
| Tamsulosin hydrochloride | 0.80 mg |
| Lactose | 7.20 mg |
| Mannitol | 10.00 mg |
| HPMC (90SH-15000) | 10.00 mg |
| Polyvinylpyrrolidone | 3.20 mg |
| Microcrystalline cellulose | 66.55 mg |
| Magnesium stearate | 1.00 mg |
| Colloidal silica | 1.25 mg |
| Total | 100.00 mg |

Step 7B: Manufacture of Particles Constituting the Layer (The Layer Containing No Drug) Used for Control of Drug Release The particles comprising the following composition units and being a layer for controlling the release of the drug are manufactured by the method mentioned in Example D-1 (Step 1B).

| | |
|---|---|
| HPMC (90SH-15000) | 121.45 mg |
| Hydrogenated castor oil | 20.56 mg |
| Yellow ferric oxide | 0.38 mg |
| Ethyl cellulose | 7.61 mg |
| Total | 150.00 mg |

Step 7D: Manufacture of a Two-Layered Tablet (Compression Molding)

A two-layered tablet is prepared by an oil press tableting machine. A pestle of 8.0 mm diameter×9.6 R is used and 1,000 kg/pestle of the tableting pressure were applied. The particles of the layer mentioned in the item of 7B are filled in a mortar and lightly tapped so that the upper surface becomes flat. A mixed powder containing a physiologically active ingredient of the layer mentioned in the item 7A is filled thereon and subjected to a compression to manufacture a two-layered tablet with an average weight of 250.00 mg and 0.80 mg of tamsulosin hydrochloride.

Test Example D (Dissolution Test)

Test Example D-1

According to the method of Test Example A, a releasing property of the preparations of Examples D1 to D18 was evaluated and the result thereof is shown in Table 13 and Table 14.

(Results and Considerations)

TABLE 13

| | Examples | | | | | | | | |
|---|---|---|---|---|---|---|---|---|---|
| | D-1 | D-2 | D-3 | D-4 | D-5 | D-6 | D-7 | D-8 | D-9 |
| Tamsulosin released at 3 h (%) | 30 | 31 | 30 | 30 | 28 | 29 | 31 | 29 | 29 |
| Tamsulosin released at 7 h (%) | 52 | 53 | 59 | 53 | 45 | 54 | 60 | 51 | 54 |
| Tamsulosin released at 12 h (%) | 76 | 74 | 85 | 76 | 63 | 77 | 89 | 70 | 77 |

TABLE 14

| | Examples | | | | | | | | |
|---|---|---|---|---|---|---|---|---|---|
| | D-10 | D-11 | D-12 | D-13 | D-14 | D-15 | D-16 | D-17 | D-18 |
| Tamsulosin released at 3 h (%) | 28 | 25 | 20 | 20 | 34 | 35 | 41 | 22 | 18 |
| Tamsulosin released at 7 h (%) | 50 | 48 | 41 | 44 | 65 | 69 | 70 | 51 | 38 |
| Tamsulosin released at 12 h (%) | 73 | 73 | 65 | — | 87 | 94 | 92 | 80 | 64 |

When a layer containing a drug is sandwiched by two release-controlling layers containing no drug to give a multi-layered tablet, a sustained release of the drug was achieved. The drug release from the present preparations can be controlled by molecular weight of HPMC used for the release-controlling layers, thickness of the release-controlling layers, addition of ethyl cellulose to the release-controlling layers, HPMC content and its molecular weight in the drug-containing layers, thickness of the drug-containing layer, geometrical shape of the drug-containing layer and diameter size of the multi-layered tablet. In addition, in all of the preparations, drug release after 7 hours from the initiation of the dissolution was between 38% and 70% and, therefore, it is a sustained-release pharmaceutical composition with similar drug release profiles obtained in Example A-2. Accordingly, it is considered that the similar pharmacokinetic parameters are obtained as those of A-2 preparation in case of the administration at the same dose, therefore, it is expected that, as compared with the current preparation, the efficacy is equivalent or better and occurrence of adverse reactions is reduced. It is also expected to increase the dose or to eliminate the restriction on ingestion of meals.

Example E

Gastroretentive Dosage Form Using Swelling Polymers

Example E-1

Powder comprising various kinds of composition units was prepared by weighing tamsulosin hydrochloride, polyethylene oxide and magnesium stearate following by fully mixing using a mortar and a pestle until being uniformity. The prepared mixed powder was charged in a mortar and subjected to compression by an oil press tableting using a pestle of 7.0 mm diameter×8.4 R with a compressing pressure of 1,000 kg/pestle to manufacture tablets with an average weight of 276.0 mg.

| | |
|---|---|
| Tamsulosin hydrochloride | 0.80 mg |
| Lactose | 7.20 mg |
| Polyethylene oxide (Polyox™ WSR N60K) | 266.00 mg |
| Magnesium stearate | 2.00 mg |
| Total | 276.00 mg |

Example E-2

A mixed powder containing tamsulosin hydrochloride and polyethylene oxide and comprising the following composition units was subjected to a compression with a pestle of 6.0 mm diameter×6.0 R according to the method mentioned Example E-1 to manufacture tablets with an average weight of 143.00 mg.

| | |
|---|---|
| Tamsulosin hydrochloride | 0.80 mg |
| Lactose | 7.20 mg |
| Polyethylene oxide (Polyox™ WSR 303) | 133.00 mg |
| Magnesium stearate | 2.00 mg |
| Total | 143.00 mg |

Example E-3

A mixed powder containing tamsulosin hydrochloride and polyethylene oxide and comprising the following composition units was subjected to a compression with a pestle of 7.0 mm diameter×8.4 R according to the method mentioned Example E-1 to manufacture tablets with an average weight of 276.00 mg.

Example E-4

A mixed powder containing tamsulosin hydrochloride and two kinds of polyethylene oxides having different molecular weight (Polyox™ WST 303 and Polyox™ WSR 1105) and comprising the following composition units was subjected to a compression with a pestle of 7.0 mm diameter×8.4 R according to the method mentioned Example 1 to manufacture tablets with an average weight of 276.00 mg.

| | |
|---|---|
| Tamsulosin hydrochloride | 0.80 mg |
| Lactose | 7.20 mg |
| Polyethylene oxide (Polyox™ WSR 303) | 133.00 mg |
| Polyethylene oxide (Polyox™ WSR 1105) | 133.00 mg |
| Magnesium stearate | 2.00 mg |
| Total | 276.00 mg |

Example E-5

A mixed powder containing tamsulosin hydrochloride, being compounded with polyethylene oxide and hydroxypropyl methylcellulose (TC5E) and comprising the following composition units was subjected to a compression with a pestle of 7.0 mm diameter×8.4 R according to the method mentioned Example E-1 to manufacture tablets with an average weight of 276.00 mg.

| | |
|---|---|
| Tamsulosin hydrochloride | 0.80 mg |
| Lactose | 7.20 mg |
| Polyethylene oxide (Polyox™ WSR 303) | 133.00 mg |
| Hydroxypropyl methylcellulose (TC5E) | 133.0 mg |
| Magnesium stearate | 2.00 mg |
| Total | 276.00 mg |

Example E-6

A mixed powder containing tamsulosin hydrochloride, being compounded with polyethylene oxide and hydroxypropyl methyl cellulose (90SH-10000) and comprising the following composition units was subjected to a compression with a pestle of 7.0 mm diameter×8.4 R according to the method mentioned Example E-1 to manufacture tablets with an average weight of 276.00 mg.

| | |
|---|---|
| Tamsulosin hydrochloride | 0.80 mg |
| Lactose | 7.20 mg |
| Polyethylene oxide (Polyox ™ WSR 303) | 133.00 mg |
| Hydroxypropyl methyl cellulose (90SH-10000) | 133.0 mg |
| Magnesium stearate | 2.00 mg |
| Total | 276.00 mg |

Test Example E (Dissolution Test)

Test Example E-1

Releasing property of the preparations of Examples E1 to E6 was evaluated according to the method of Test Example A and the result is shown in Table 15.

(Results and Considerations)

TABLE 15

|  | Examples | | | | | |
| --- | --- | --- | --- | --- | --- | --- |
|  | E-1 | E-2 | E-3 | E-4 | E-5 | E-6 |
| Tamsulosin released at 3 h (%) | 25 | 28 | 19 | 22 | 27 | 21 |
| Tamsulosin released at 7 h (%) | 62 | 66 | 43 | 55 | 60 | 46 |
| Tamsulosin released at 12 h (%) | 91 | 92 | 71 | 92 | 86 | 70 |

As a result of making into intragastrically retaining preparation using a swelling polymer, sustained release of the drug was achieved. Drug release from the present preparations can be controlled by molecular weight and loading amount of polyethylene oxide and a combination of a plurality of water-soluble polymers. Drug release after 7 hours from initiation of the dissolution was between 43% and 66% in all preparations. Therefore, they were sustained-release pharmaceutical compositions with similar drug release profiles obtained in Example A-2. Accordingly, it is considered that the similar pharmacokinetic parameters are obtained as those of A-2 preparation in case of the administration at the same dose, therefore, it is expected that, as compared with the current preparation, the efficacy is equivalent or better and occurrence of adverse reactions is reduced. It is also expected to increase the dose or to eliminate the restriction on ingestion of meals.

Example F

Matrix Preparation Using Water-Soluble Polymers

Example F-1

Manufacture of a Hydroxypropyl Methylcellulose (HPMC) Matrix Tablet Containing Tamsulosin Hydrochloride Step 1A: Manufacture of Mixed Powder Containing an Active Ingredient A mixed powder containing 0.80 mg of tamsulosin hydrochloride and comprising the following composition units was manufactured.

| Tamsulosin hydrochloride | 0.80 mg |
| --- | --- |
| Lactose | 149.20 mg |
| Hydroxypropyl methylcellulose (60SH-10000) | 200.00 mg |
| Total | 350.00 mg |

The powder comprising the above-mentioned composition units was prepared by weighing necessary amounts of an active ingredient, mannitol and hydroxypropyl methyl cellulose (HPMC 60SH-10000) followed by well mixing using a mortar and a pestle until being uniformity.

Step 1B: Manufacture of HPMC Matrix (Compression Molding)

HPMC matrix tablet is prepared using an oil press tableting machine. A pestle of 9.5 mm diameter×11.4 R was used and 500 kg/pestle of the compressing pressure was applied. A mixed powder containing the active ingredient mentioned in the item 1A is charged and subjected to a compression to manufacture a matrix tablet with an average weight of 350.00 mg and containing 0.80 mg of tamsulosin hydrochloride.

Example F-2

Manufacture of HPMC Matrix Tablet Containing Tamsulosin Hydrochloride

Step 2A: Manufacture of Mixed Powder Containing an Active Ingredient

A mixed powder containing 0.80 mg of tamsulosin hydrochloride and comprising the following composition units is manufactured according to the method mentioned in Example F-1 (Step 1A).

| Tamsulosin hydrochloride | 0.80 mg |
| --- | --- |
| Lactose | 149.20 mg |
| HPMC (90SH-4000) | 200.00 mg |
| Total | 350.00 mg |

Step 2B: Manufacture of HPMC Matrix Tablet (Compression Molding)

A matrix tablet with an average weight of 350.00 mg and containing 0.80 mg of tamsulosin hydrochloride is manufactured according to the method mentioned in Example F-1 (step 1B).

Example F-3

Manufacture of HPMC Matrix Tablet Containing Tamsulosin Hydrochloride

Step 3A: Manufacture of Mixed Powder Containing an Active Ingredient

A mixed powder containing 0.80 mg of tamsulosin hydrochloride and comprising the following composition units is manufactured according to the method mentioned in Example F-1 (step 1A).

| Tamsulosin hydrochloride | 0.80 mg |
| --- | --- |
| Lactose | 149.20 mg |
| HPMC (90SH-100000) | 200.00 mg |
| Total | 350.00 mg |

Step 3B: Manufacture of HPMC Matrix Tablet (Compression Molding)

A matrix tablet with an average weight of 350.00 mg and containing 0.80 mg of tamsulosin hydrochloride is manufactured according to the method mentioned in Example F-1 (step 1B).

Example F-4

Manufacture of HPMC Matrix Tablet Containing Tamsulosin Hydrochloride

Step 4A: Manufacture of Mixed Powder Containing an Active Ingredient

A mixed powder containing 0.80 mg of tamsulosin hydrochloride and comprising the following composition units is manufactured according to the method mentioned in Example F-1 (Step 1A).

| | |
|---|---|
| Tamsulosin hydrochloride | 0.80 mg |
| Lactose | 49.20 mg |
| HPMC (90SH-15000) | 350.00 mg |
| Total | 400.00 mg |

Step 4B: Manufacture of HPMC Matrix Tablet (Compression Molding)

A matrix tablet with an average weight of 400.00 mg and containing 0.80 mg of tamsulosin hydrochloride is manufactured according to the method mentioned in Example F-1 (step 1B).

Example F-5

Manufacture of HPMC Matrix Tablet Containing Tamsulosin Hydrochloride

Step 5A: Manufacture of Mixed Powder Containing an Active Ingredient

A mixed powder containing 0.80 mg of tamsulosin hydrochloride and comprising the following composition units is manufactured according to the method mentioned in Example F-1 (step 1A).

| | |
|---|---|
| Tamsulosin hydrochloride | 0.80 mg |
| Lactose | 249.20 mg |
| HPMC (60SH-10000) | 100.00 mg |
| Total | 350.00 mg |

Step 5B: Manufacture of HPMC Matrix Tablet (Compression Molding)

A matrix tablet with an average weight of 350.00 mg and containing 0.80 mg of tamsulosin hydrochloride is manufactured according to the method mentioned in Example F-1 (step 1B).

Example F-6

Manufacture of HPMC Matrix Tablet Containing Tamsulosin Hydrochloride

Step 6A: Manufacture of Mixed Powder Containing an Active Ingredient

A mixed powder containing 0.80 mg of tamsulosin hydrochloride and comprising the following composition units is manufactured according to the method mentioned in Example F-1 (Step 1A).

| | |
|---|---|
| Tamsulosin hydrochloride | 0.80 mg |
| Lactose | 199.20 mg |
| HPMC (60SH-10000) | 150.00 mg |
| Total | 350.00 mg |

Step 6B: Manufacture of HPMC Matrix Tablet (Compression Molding)

A matrix tablet with an average weight of 350.00 mg and containing 0.80 mg of tamsulosin hydrochloride is manufactured according to a method mentioned in Example F-1 (step 1B).

Example F-7

Manufacture of HPMC Matrix Tablet Containing Tamsulosin Hydrochloride

Step 7A: Manufacture of Mixed Powder Containing an Active Ingredient

A mixed powder containing 0.80 mg of tamsulosin hydrochloride and comprising the following composition units is manufactured according to the method mentioned in Example F-1 (step 1A).

| | |
|---|---|
| Tamsulosin hydrochloride | 0.80 mg |
| Lactose | 49.20 mg |
| HPMC (60SH-10000) | 300.00 mg |
| Total | 350.00 mg |

Step 6B: Manufacture of HPMC Matrix Tablet (Compression Molding)

A matrix tablet with an average weight of 350.00 mg and containing 0.80 mg of tamsulosin hydrochloride is manufactured according to the method mentioned in Example F-1 (step 1B).

Test Example F(Dissolution Test)

Test Example F-1

Releasing property of the preparations of Examples F1 to F7 was evaluated according to the method of Test Example A and the result is shown in Table 16.

(Results and Considerations)

TABLE 16

| | Examples | | | | | | |
|---|---|---|---|---|---|---|---|
| | F-1 | F-2 | F-3 | F-4 | F-5 | F-6 | F-7 |
| Tamsulosin released at 3 h (%) | 28 | 33 | 34 | 21 | 53 | 40 | 16 |
| Tamsulosin released at 7 h (%) | 56 | 62 | 60 | 44 | 85 | 72 | 38 |
| Tamsulosin released at 12 h (%) | 79 | 87 | 81 | 66 | 100 | 95 | 62 |

As a result of using hydroxypropyl methylcellulose (HPMC) as a water-soluble polymer, a sustained release of the drug was achieved. Drug release after 7 hours from initiation of the dissolution was between 38% and 85% in all preparations and, therefore, they were sustained-release pharmaceutical compositions with similar drug release profiles obtained in Example A-2. Accordingly, it is considered that the similar pharmacokinetic parameters are obtained as those of A-2 preparation in case of the administration at the same dose, therefore, it is expected that, as compared with the current preparation, the efficacy is equivalent or better and occurrence of adverse events is reduced. It is also expected to increase the dose or to eliminate the restriction on ingestion of meals.

Experimental Example 1

Comparison of the Current Preparation with the Present Invention Preparation in a Single Administration The current preparation (Flomax (registered trade mark)) or the preparation of Example A-2 was orally administered to healthy male volunteers before ingestion of meal (under a fast condition) at a dose of 0.4 mg once daily. After the administration, blood samples were collected periodically, plasma tamsulosin concentrations were determined and the ratio ($C_{min}/C_{max}$) of the plasma tamsulosin concentration at 24 hours after the administration ($C_{min}$) to the maximum plasma tamsulosin concentration ($C_{max}$) was calculated and shown in Table 17.

after ingestion of meal, blood samples were collected periodically after the administration on day 5. After that the plasma tamsulosin concentrations were determined. The maximum plasma tamsulosin concentration ($C_{max}$) and the plasma tamsulosin concentration at 24 hours after the administration ($C_{min}$) were determined and the ratio of $C_{min}$ to $C_{max}$ ($C_{min}/C_{max}$) was calculated and shown in Table 18.

(Results and Considerations)

TABLE 18

|  | Current Preparation | | Preparation of Example A-2 | |
| --- | --- | --- | --- | --- |
|  | Administered before ingestion of meal | Administered after ingestion of meal | Administered before ingestion of meal | Administered after ingestion of meal |
| $C_{min}$ | 4.0 ± 2.6 ns | 3.8 ± 2.5 | 4.6 ± 3.6 ns | 4.8 ± 2.7 |
| $C_{max}$ | 17.1 ± 7.3** | 10.1 ± 4.8 | 10.7 ± 5.5 ns | 11.1 ± 3.7 |
| $C_{min}/C_{max}$ | 0.222 ± 0.015** | 0.355 ± 0.113 | 0.404 ± 0.0144 ns | 0.421 ± 0.116 | ns: No significant difference was noted from the administration after ingestion of meal.
**Significant difference was noted from the administration under a fed condition ($p < 0.01$).

(Results and Considerations)

TABLE 17

|  | Current Preparation | Preparation of Example A-2 |
| --- | --- | --- |
| $C_{min}/C_{max}$ | 0.161 ± 0.073** | 0.709 ± 0.180 |

**Statistically significant difference was noted between the current preparation and the preparation of example A-2 ($p < 0.01$)

When the current preparation was administered, the average value of $C_{min}/C_{max}$ was 0.161 while, when the preparation of the present invention was administered, that was 0.709. Accordingly, it was noted that control of the tamsulosin release from the preparation is useful for maintaining the effective plasma concentrations.

Many of postural hypotension, which is often noted upon administration of an α receptor blocking agent, is thought to transitionally occur as a result of a rapid increase in the plasma concentrations at the initial phase after the administration. Accordingly, making the $C_{min}/C_{max}$ large whereby the plasma concentrations are made constant is useful not only in reducing the occurrence of adverse reactions but also in sustaining the efficacy and it is thought that the preparation satisfying the above can be administered at high doses. The $C_{min}/C_{max}$ of the A-2 preparation in a single administration is significantly larger than that of the current preparation ($p < 0.01$) and, as compared with the current preparation, reduction in occurrence of the adverse reactions and sustaining of the efficacy can be expected.

Experimental Example 2

Comparison of the Current Preparation with the Present Invention Preparations in a Repeated Administration Before ingestion of meal (a fast condition) or after ingestion of meal, the current preparation (Omnic/Flomax (registered trade marks)) or the preparation of Example A-2 was administered per os to healthy male volunteers at a dose of 0.4 mg once daily for at least five days repeatedly. For current preparation, blood samples were collected periodically after the administration on day 7 for the "before ingestion of meal" condition or on day 6 for the "after ingestion of meal" condition. For the administration of A-2 preparation before and With regard to $C_{max}$, a significant increase was observed before ingestion of meal in the current preparation compared to that after ingestion of meal ($p < 0.01$) while, in case of the A-2 preparation, no significant influence by meal was noted. Further, in the current preparation before ingestion of meal, the ratio of $C_{min}/C_{max}$ significantly decreased compared to that after ingestion of meal ($p < 0.01$) while, in case of the A-2 preparation, no significant difference was noted regardless of the meal conditions. Still further, the $C_{min}/C_{max}$ in the current preparation under a fed condition was small as compared with that in the A-2 preparation. From the above result, it is thought that the A-2 preparation is not affected by food and that, as compared with the current preparation, it improves compliance, reduces the frequency of occurrence of adverse reactions and, moreover, can be expected to sustain the efficacy. Accordingly, it is now shown that making the ratio of $C_{min}/C_{max}$ more than about 0.4 is useful in the design of tamsulosin preparations which are difficult to be affected by the meal conditions.

Experimental Example 3

Adverse Event Profiles in Clinical Test in Phase-III

In the clinical investigation to female patients of 18 to 70 years age where symptoms of overactive bladder (urinary frequency, urgency or urinary urge) have continued for three months or longer, the preparations of the present invention (Examples A-4, 5 and 6) were orally administered once daily at the doses of 0.25 mg to 1.5 mg per day for six weeks. As a result, the adverse event profiles of the group to which 1.5 mg of tamsulosin hydrochloride was administered as a sustained-released preparation of the present invention was not significantly different from those of the group to which placebo was administered. Accordingly, it is shown that, in an oral administration of a tamsulosin preparation, controlling of the pharmacokinetic parameters within a specific range is effective in making it possible to administer the preparation at a high dose without increasing the frequency of occurrence of adverse reactions.

Experimental Example 4

Adverse Event Profiles in Clinical Test in Phase-III

Placebo was orally administered to male patients with lower uropathy symptoms for two weeks and, after that, the current preparation or the preparation of Example A-2 was orally administered at a dose of 0.4 mg once daily for 12 weeks. The test was carried out by means of a double blind test and expression of adverse reactions was investigated.
(Results and Considerations)

As a result of comparison of the group to which the A-2 preparation was administered with the group to which the current preparation was administered, adverse event profiles of the group to which the A-2 preparation was administered was improved as compared with those of the group to which the current preparation was administered, and in particular, the effect was remarkable on abnormal ejaculation and postural hypotension. Accordingly, it has been shown that, in an oral administration of a tamsulosin preparation, controlling of the pharmacokinetic parameters within a specific range is effective in order to reduce the frequency of occurrence of adverse reactions.

INDUSTRIAL APPLICABILITY

As compared with the current oral sustained-released preparation containing tamsulosin hydrochloride which have been supplied to the clinical setting, the sustained-released pharmaceutical composition and a method of the present invention have equivalent or even more efficacy and, in addition, they decrease adverse events such as adverse reactions (e.g. postural hypotension). They are also useful as excellent sustained-release preparations for oral use and method where dose can be increased and there is no restriction for ingestion of meal.

(i) Determination Method of Tamsulosin hydrochloride in Plasma:

After adding 0.5 ml of an aqueous solution of internal standard substance (containing 0.5 .mu·g of amosulalol hydrochloride) to 1.5 ml of plasma, 1 ml of a saturated aqueous solution of sodium hydrogencarbonate was added thereto and the active substance was extracted with 4 ml of ethyl acetate. The ethyl acetate extract was further extracted with 2.5 ml of 0.4N hydrochloric acid. The hydrochloric acid layer thus obtained was adjusted to weak alkaline by the addition of 2 ml of a saturated aqueous solution of sodium hydrogencarbonate and then re-extracted with 4 ml of ethyl acetate. The ethyl acetate layer thus obtained was distilled under reduced pressure and after adding 0.05 ml of an aqueous solution of 0.1 M sodium hydrogencarbonate and 0.1 ml of an acetone solution of 500 μg of dansyl chloride, the reaction was performed for 120 minutes at 35 ° C. After adding 4 ml of ether to the reaction mixture, the organic layer thus formed was washed with 5 ml of water and then with 5 ml of an aqueous solution of 0.2N hydrochloric acid. The solvent was distilled off from the organic layer, the residue thus formed was dissolved in 0.05 ml of the mixed liquid for the mobile phase of the following operation condition, and using all of the solution the active substance was determined by a liquid chromatography under the following operation condition.

The retention times for dansyl-tamsulosin and dansyl-amosulalol when the flow rate of the eluent was 1.4 ml/min. were 8.1 minutes and 12.5 minutes, respectively.

Operation Condition:

Detector: Fluorescent Photometer (Excitation wavelength 365 nm, fluorescent wavelength 500 nm)

Column: In a stainless tube of about 4 mm in inside diameter and about 250 mm in length was packed by about 5 .mu·m of silica gel (e.g., Lichrosorb SI 100, trade name, made by Merck & Co., Ltd.) as a filler.

Column Temperature: About 10 ° C.

Mobile Phase: Mixture of benzene and methanol (100:1).

Flow Rate: Constant flow rate of 1.2 to 1.9 ml per minute.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for maintaining an effective plasma concentration of tamsulosin or a pharmaceutically acceptable salt thereof in an individual while reducing postural hypotension, said method comprising:

orally administering a pharmaceutical composition containing tamsulosin or a pharmaceutically acceptable salt thereof and a carrier for a sustained-release pharmaceutical composition, wherein said composition is a member selected from the group consisting of; (B) a preparation of an osmotic pump formulation comprising a two-layered compressed core containing tamsulosin or a pharmaceutically acceptable salt thereof containing a poly(alkylene oxide) polymer with a number average molecular weight of 100,000 to 750,000 and a push layer containing a poly(alkylene oxide) polymer with a number average molecular weight of 1,000,000 to 15,000,000 coated with a semipermeable membrane containing a member selected from the group consisting of a cellulose ester, a cellulose ether and a cellulose ester-ether;

(C) a gel preparation in which a plurality of gums are combined comprising a hetero polysaccharide gum selected from the group consisting of xanthan gum and a xanthan gum derivative selected from a deacylated xanthan gum, a carboxymethyl ether and propylene glycol ester and a homo polysaccharide gum, which is locust bean, a water-soluble cationic cross-linking agent, an inert diluent, and ethyl cellulose; (D) a multi-layered tablet preparation comprising 3 layers, i) a first layer comprising a mixture or granules containing 5 to 90 w/w % of a water-soluble polymer in the first layer and having a property of being swollen by contact to environmental fluids and ethyl cellulose;

ii) a second layer comprising a water-soluble polymer of hydroxymethylcellulose, auxiliary substances of microcrystalline cellulose and polyvinylpyrrolidone and containing tamsulosin or a pharmaceutically acceptable salt thereof which is adjacent to the first layer and, iii) a third layer being adhered to the second layer which comprises ethyl cellulose and a water-soluble polymer which is gelled and/or swollen followed by free disintegration, wherein said water-soluble polymer in the first, second and third layers can be the same or different and is a member selected from the group consisting of hydroxymethyl cellulose, hydroxyethyl cellulose, hydroxypropyl methyl cellulose and hydroxypropyl cellulose; and wherein even for 8 to 24 hours after administering, said composition selected from the group consisting of B, C, and D, still releases tamsulosin to be absorbed in vivo; and maintaining an effective plasma concentration of tamsulosin or a pharmaceutically acceptable salt thereof, said effective plasma concentration indicated by a ratio ($C_{min}/C_{max}$ ratio) of the plasma tamsulosin concentration at 24 hours after the administration of the preparation per os ($C_{min}$) to the maximum plasma tamsulosin concentration after the administration ($C_{max}$) being about 0.4 to less than about 1 in said individual to reduce postural hypotension.

2. The method according to claim 1, wherein a value of $C_{min}$ normalized by the dose of tamsulosin or a pharmaceutically acceptable salt thereof is more than about $10 \times 10^{-6}$ $mL^{-1}$.

3. The method according to claim 1, wherein $C_{min}$ is about 4 ng/mL or more.

4. The method according to claim 1, wherein a value of $C_{max}$ normalized by the dose of tamsulosin or a pharmaceutically acceptable salt thereof is about $40 \times 10^{-6}$ $mL^{-1}$ or less.

5. The method according to claim 1, wherein a value of $C_{max}$ normalized by the dose of tamsulosin or a pharmaceutically acceptable salt thereof is about $30 \times 10^{-6}$ $mL^{-1}$ or less.

6. The method according to claim 1, wherein a value of $C_{max}$ is about 20 ng/mL or less.

7. The method according to claim 1, wherein its adverse event profiles are not significantly different from those of placebo.

8. The method according to claim 1, wherein, when it is administered before ingestion of food or after ingestion of food, there is no significant difference in pharmacokinetic parameters obtained from plasma tamsulosin concentration profiles.

9. The method according to claim 1, wherein tamsulosin hydrochloride is given at 0.1 to 2 mg per day.

10. The method according to claim 1, wherein tamsulosin hydrochloride is given at 0.4 to 0.8 mg per day.

11. The method according to claim 1, wherein said tamsulosin or a pharmaceutically acceptable salt thereof is tamsulosin hydrochloride.

12. The method according to claim 1, wherein said formulation is said preparation of an osmotic pump formulation comprising a two-layered compressed core containing tamsulosin or a pharmaceutically acceptable salt thereof containing a poly(alkylene oxide) polymer with a number average molecular weight of 100,000 to 750,000 and a push layer containing a poly(alkylene oxide) polymer with a number average molecular weight of 1,000,000 to 15,000,000 coated with a semipermeable membrane containing a member selected from the group consisting of a cellulose ester, a cellulose ether and a cellulose ester-ether.

13. The method according to claim 1, wherein said formulation is said gel preparation in which a plurality of gums are combined comprising a hetero polysaccharide gum selected from the group consisting of xanthan gum and a xanthan gum derivative selected from a deacylated xanthan gum, a carboxymethyl ether and propylene glycol ester and a homo polysaccharide gum, which is locust bean, a water-soluble cationic cross-linking agent, an inert diluent, and ethyl cellulose.

14. The method according to claim 1, wherein said formulation is said multi-layered tablet preparation comprising 3 layers,
  i) a first layer comprising a mixture or granules containing 5 to 90 w/w % of a water-soluble polymer in the first layer and having a property of being swollen by contact to environmental fluids and ethyl cellulose;
  ii) a second layer comprising a water-soluble polymer of hydroxymethylcellulose, auxiliary substances of microcrystalline cellulose and polyvinylpyrrolidone and containing tamsulosin or a pharmaceutically acceptable salt thereof which is adjacent to the first layer and,
  iii) a third layer being adhered to the second layer which comprises ethyl cellulose and a water-soluble polymer which is gelled and/or swollen followed by free disintegration, wherein said water-soluble polymer in the first, second and third layers can be the same or different and is a member selected from the group consisting of hydroxymethyl cellulose, hydroxyethyl cellulose, hydroxypropyl methyl cellulose and hydroxypropyl cellulose.

* * * * *

UNITED STATES PATENT AND TRADEMARK OFFICE
CERTIFICATE OF CORRECTION

| | | |
|---|---|---|
| PATENT NO. | : 8,128,958 B2 | Page 1 of 1 |
| APPLICATION NO. | : 10/843005 | |
| DATED | : March 6, 2012 | |
| INVENTOR(S) | : Sako et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1145 days.

Signed and Sealed this
Nineteenth Day of June, 2012

David J. Kappos
*Director of the United States Patent and Trademark Office*